US011826509B2

(12) United States Patent
Nelson et al.

(10) Patent No.: US 11,826,509 B2
(45) Date of Patent: Nov. 28, 2023

(54) RESPIRATORY USER INTERFACE

(71) Applicant: Fisher & Paykel Healthcare Limited, Auckland (NZ)

(72) Inventors: Grant Leigh Nelson, Auckland (NZ); Carsten Ma On Wong Corazza, Auckland (NZ); Stanislav Tatkov, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 571 days.

(21) Appl. No.: 16/615,751

(22) PCT Filed: May 22, 2018

(86) PCT No.: PCT/NZ2018/050070
§ 371 (c)(1),
(2) Date: Nov. 21, 2019

(87) PCT Pub. No.: WO2018/217103
PCT Pub. Date: Nov. 29, 2018

(65) Prior Publication Data
US 2020/0101250 A1 Apr. 2, 2020

Related U.S. Application Data

(60) Provisional application No. 62/509,507, filed on May 22, 2017.

(51) Int. Cl.
*A61M 16/06* (2006.01)
*A61M 16/08* (2006.01)
*A61M 16/16* (2006.01)

(52) U.S. Cl.
CPC .... *A61M 16/0616* (2014.02); *A61M 16/0666* (2013.01); *A61M 16/0816* (2013.01); *A61M 16/16* (2013.01)

(58) Field of Classification Search
CPC .............. A61M 16/00; A61M 16/0605; A61M 16/0611; A61M 16/0616; A61M 16/0622;
(Continued)

(56) References Cited

U.S. PATENT DOCUMENTS

| 1,896,716 A | 2/1933 | McKesson |
|---|---|---|
| 2,156,852 A | 5/1939 | Horak |

(Continued)

FOREIGN PATENT DOCUMENTS

| AU | 2010335069 | 6/2011 |
|---|---|---|
| CN | 101489617 | 7/2009 |

(Continued)

OTHER PUBLICATIONS

International Search Report; PCT/NZ2018/050070; dated Aug. 13, 2018; 11 pages.

(Continued)

*Primary Examiner* — Margaret M Luarca
(74) *Attorney, Agent, or Firm* — Knobbe Martens Olson and Bear, LLP

(57) ABSTRACT

There is provided a user interface comprising: a. a mask body; b. a sealing cushion connected to the mask body and configured to seal around a patient's nose and/or mouth; wherein the mask body and sealing cushion together define an interior chamber of the user interface; c. a breathing gas delivery inlet provided in the mask body and configured to receive a breathing gas flow from a gas source; and d. at least one non-sealing nasal prong in the interior chamber. The user interface further comprising a breathing gas flow director configured to split the breathing gas flow into two flow paths such that a portion of the breathing gas flow is delivered along a first flow path from the inlet into the interior chamber to pressurise the interior chamber, and such (Continued)

that a portion of the breathing gas flow is delivered along a second flow path from the inlet through the nasal prong.

20 Claims, 28 Drawing Sheets

(58) Field of Classification Search
CPC .......... A61M 16/0666; A61M 16/0672; A61M 16/0045; A61M 2202/0225; A61M 16/0816

See application file for complete search history.

(56) References Cited

U.S. PATENT DOCUMENTS

| | | | |
|---|---|---|---|
| 2,313,999 A | 3/1943 | Kreiselman | |
| 2,341,566 A | 2/1944 | Monro | |
| 2,375,803 A | 5/1945 | Chase et al. | |
| 2,663,297 A | 12/1953 | Turnberg | |
| 2,675,803 A | 4/1954 | Kaslow | |
| 2,693,800 A | 11/1954 | Caldwell | |
| 2,868,199 A | 1/1959 | Hudson | |
| 3,330,274 A | 7/1967 | Bennett | |
| 3,513,844 A | 5/1970 | Smith | |
| 4,201,205 A | 5/1980 | Bartholomew | |
| 4,231,363 A | 11/1980 | Grimes | |
| 4,248,218 A | 2/1981 | Fischer | |
| 4,328,767 A | 2/1982 | Peterson | |
| 4,328,797 A | 5/1982 | Rollins, III et al. | |
| 4,354,488 A | 10/1982 | Bartos | |
| 4,944,310 A | 7/1990 | Sullivan | |
| 5,005,571 A | 4/1991 | Dietz | |
| 5,400,781 A | 3/1995 | Davenport | |
| 5,474,060 A | 12/1995 | Evans | |
| 6,357,437 B1 | 3/2002 | Jacques | |
| 6,418,928 B1 * | 7/2002 | Bordewick ....... A61M 16/0616 128/207.18 |
| 6,561,190 B1 | 5/2003 | Kwok | |
| 6,679,265 B2 | 1/2004 | Strickland et al. | |
| 7,255,107 B1 | 8/2007 | Gomez | |
| 7,341,059 B2 | 3/2008 | Moody et al. | |
| 7,406,966 B2 | 8/2008 | Wondka | |
| 7,493,902 B2 | 2/2009 | White et al. | |
| 7,559,327 B2 | 7/2009 | Hernandez | |
| 7,958,889 B1 | 6/2011 | Fernandez-DeCastro | |
| 8,342,179 B2 | 1/2013 | Hacke et al. | |
| 8,844,530 B2 | 9/2014 | Birnkrant | |
| 9,032,955 B2 | 5/2015 | Lubke et al. | |
| 10,556,079 B2 | 2/2020 | Tatkov | |
| 11,185,653 B2 | 11/2021 | O'Donnell et al. | |
| 2002/0053347 A1 | 5/2002 | Ziaee | |
| 2002/0112730 A1 | 8/2002 | Dutkiewicz | |
| 2002/0122746 A1 | 9/2002 | Yamamori et al. | |
| 2003/0024533 A1 | 2/2003 | Sniadach | |
| 2003/0168063 A1 | 9/2003 | Gambone et al. | |
| 2004/0261797 A1 | 12/2004 | White et al. | |
| 2005/0011523 A1 | 1/2005 | Aylsworth et al. | |
| 2005/0028822 A1 | 2/2005 | Sleeper et al. | |
| 2005/0066976 A1 | 3/2005 | Wondka | |
| 2005/0098183 A1 | 5/2005 | Nash | |
| 2006/0081243 A1 | 4/2006 | McDonald et al. | |
| 2006/0169281 A1 | 8/2006 | Aylsworth et al. | |
| 2006/0266361 A1 | 11/2006 | Hernande | |
| 2006/0278233 A1 | 12/2006 | McAuley et al. | |
| 2007/0079982 A1 | 4/2007 | Laurent et al. | |
| 2007/0089749 A1 | 4/2007 | Ho et al. | |
| 2007/0107737 A1 | 5/2007 | Landis et al. | |
| 2007/0113848 A1 | 5/2007 | Acker et al. | |
| 2007/0113856 A1 | 5/2007 | Acker et al. | |
| 2007/0125380 A1 | 6/2007 | Acker et al. | |
| 2007/0125385 A1 | 6/2007 | Ho et al. | |
| 2007/0144518 A1 | 6/2007 | Acker et al. | |
| 2008/0060653 A1 | 3/2008 | Hallett et al. | |
| 2008/0078389 A1 | 4/2008 | Xiao et al. | |
| 2008/0276937 A1 | 11/2008 | Davidson et al. | |
| 2008/0295846 A1 | 12/2008 | Han et al. | |
| 2008/0319334 A1 | 12/2008 | Yamamori | |
| 2009/0000618 A1 | 1/2009 | Warren | |
| 2009/0101147 A1 | 4/2009 | Landis et al. | |
| 2009/0173349 A1 | 7/2009 | Hernandez et al. | |
| 2009/0250060 A1 | 10/2009 | Hacke et al. | |
| 2011/0009763 A1 | 1/2011 | Levitzky et al. | |
| 2011/0067704 A1 | 3/2011 | Kooij et al. | |
| 2012/0055480 A1 | 3/2012 | Wilkinson | |
| 2012/0125338 A1 | 5/2012 | Yarahmadi | |
| 2012/0167892 A1 | 7/2012 | Matula | |
| 2012/0240935 A1 | 9/2012 | Johansen | |
| 2012/0285448 A1 | 11/2012 | Dugan et al. | |
| 2012/0305001 A1 * | 12/2012 | Tatkov ................ A61M 16/109 128/205.25 |
| 2013/0213400 A1 | 8/2013 | Barlow et al. | |
| 2014/0096773 A1 | 4/2014 | Amarasinghe | |
| 2014/0107517 A1 | 4/2014 | Hussain | |
| 2014/0166015 A1 | 6/2014 | Waggoner | |
| 2014/0246025 A1 | 9/2014 | Gragg et al. | |
| 2015/0217074 A1 | 8/2015 | Wells | |
| 2016/0022948 A1 * | 1/2016 | Martin ............. A61M 16/0672 128/205.25 |
| 2016/0082215 A1 | 3/2016 | Bugamelli et al. | |
| 2016/0282215 A1 | 9/2016 | Naito et al. | |
| 2016/0296720 A1 * | 10/2016 | Henry ............. A61M 16/0875 |
| 2016/0339195 A1 | 11/2016 | Raje et al. | |
| 2017/0182275 A1 | 1/2017 | O'Donnell et al. | |
| 2017/0128689 A1 * | 5/2017 | Law .................. A61M 16/0683 |
| 2017/0173291 A1 * | 6/2017 | Pedro ................ A61M 16/0605 |
| 2019/0351168 A1 | 11/2019 | Tatkov | |
| 2020/0010250 A1 | 1/2020 | Herling et al. | |
| 2022/0096772 A1 | 3/2022 | O'Donnell et al. | |

FOREIGN PATENT DOCUMENTS

| | | |
|---|---|---|
| CN | 202590116 | 12/2012 |
| CN | 103405843 | 11/2013 |
| EP | 0747078 | 10/2002 |
| EP | 1484075 | 12/2004 |
| EP | 1800707 | 6/2007 |
| EP | 1334742 | 4/2008 |
| EP | 2515984 | 10/2012 |
| EP | 3556418 | 10/2019 |
| EP | 3808399 | 4/2021 |
| JP | 2009-512510 | 3/2009 |
| JP | 2013-507205 | 3/2013 |
| JP | 2013-515560 | 5/2013 |
| WO | WO 82/03548 | 10/1982 |
| WO | WO 2005/018524 | 3/2005 |
| WO | WO 2005/063328 | 7/2005 |
| WO | WO 2008/031149 | 3/2008 |
| WO | WO 2009/109005 | 9/2009 |
| WO | WO 2010/057166 | 5/2010 |
| WO | WO 2010/076704 A1 | 7/2010 |
| WO | WO 2011/030250 | 3/2011 |
| WO | WO 2011/078702 | 6/2011 |
| WO | WO 2011/078703 | 6/2011 |
| WO | WO 2015/145390 | 3/2015 |
| WO | WO 2016/041019 A1 | 3/2016 |
| WO | WO 2016/201358 A1 | 12/2016 |
| WO | WO-2016201358 A1 * | 12/2016 ............. A61B 5/082 |
| WO | WO 2017/011864 | 1/2017 |
| WO | WO 2017/011864 A1 | 1/2017 |

OTHER PUBLICATIONS

International Preliminary Report on Patentability for International Application No. PCT/NZ2018/050070 dated Nov. 26, 2019.
Australian Patent Examination Report for Patent Application No. 2010335069 dated Apr. 30, 2015, 6 pages.
European Supplementary Search Report for Application No. for PCT/NZ2010000260 dated Feb. 26, 2015, 5 pages.
SIPO Notification of First Office Action (PCT in National Phase) for Application No. 201080063516.0 dated May 6, 2014, 7 pages.
SIPO Second Office Action for Application No. 201080063516.0 dated Feb. 17, 2015, 4 pages.

(56) References Cited

OTHER PUBLICATIONS

International Search Report for International Application No. PCT/NZ2010/000260; dated Apr. 27, 2011; 6 pages.
Http://en.wikipedia.org/wiki/Oxygen_therapy. Viewed on Jan. 29, 2021.

* cited by examiner

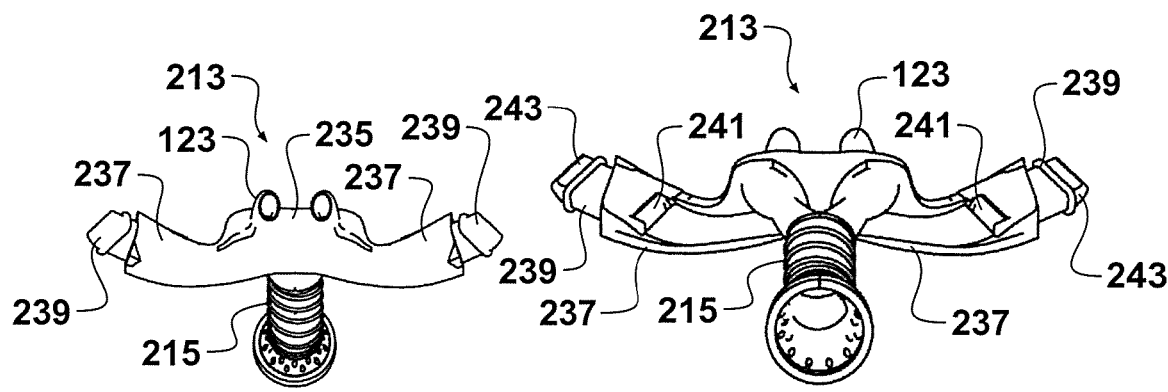
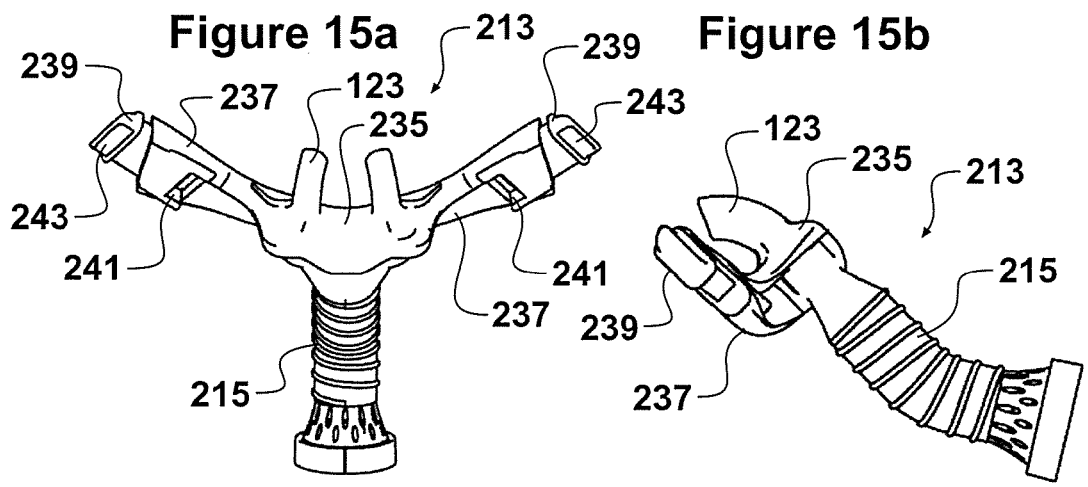
Figure 15a
Figure 15b
Figure 15c
Figure 15d

RESPIRATORY USER INTERFACE

BACKGROUND OF THE DISCLOSURE

Field of the Disclosure

The present invention generally relates to a respiratory user interface for use with, or comprising part of, a respiratory therapy system. The present invention stems from work based on the disclosure of our earlier applications, published as WO2011078703 and WO2015130179, the entire contents of each of which are incorporated herein by reference. This application claims priority from provisional application U.S. 62/509,507 filed 22 May 2017, the entire contents of which is also incorporated herein by reference.

Description of the Related Art

A respiratory therapy system typically delivers heated and humidified gases for various medical or therapy procedures, including respiratory treatment, laparoscopy and the like. Such a system can be configured to control temperature, humidity and flow rates. Respiratory humidification can also be used in respiratory therapy systems.

A respiratory therapy system is typically used for the treatment of respiratory conditions such as, for example, obstructive sleep apnea (OSA) or chronic obstructive pulmonary disease (COPD). This disclosure relates to any respiratory therapy system, for treatment of any respiratory condition.

A respiratory therapy system includes an inspiratory flow path along which breathing gas is delivered from a gas source to the patient, and an expiratory flow path along which expiratory gas flows from the patient. The inspiratory and expiratory flow paths may be the same, but are typically different. Examples of a gas source include a source of pressurised gas, or a ventilator comprising a blower (typically comprising an impeller and a motor). This flow path is typically referred to as the breathing circuit. The components that define the inspiratory part of the breathing circuit are known as the inspiratory limb of the system, and typically comprise one or more sections of inspiratory gas delivery conduit and one or more connectors that connect the section(s) of conduit between the source of breathing gas and a user interface that delivers the breathing gas to the patient. A humidifier may be provided between the gas source and the breathing circuit to humidify the breathing gas.

One method of treating respiratory distress and certain respiratory disorders (including Chronic Obstructive Pulmonary Disease or COPD and Obstructive Sleep Apnea or OSA) is the provision of Continuous Positive Airway Pressure (CPAP) or other forms of Positive Airway Pressure (PAP) to support a user's respiratory system. Non-invasive respiratory pressurization or non-invasive ventilation (NIV) is commonly administered by delivering pressurised breathing gases to a user's mouth and/or nose.

Conventional user interfaces are configured to form a seal with the user's face or upper airway to facilitate adequate pressurization of the user's respiratory system. Forma™, Oracle™, Zest™ and Opus™ are examples of sealing respiratory user interfaces produced by Fisher & Paykel Healthcare Limited. These interfaces are configured to seal with a user's face, mouth, nose and nares respectively. These interfaces comprise a mask body and sealing cushion. Typically the mask body is more rigid than the cushion, and includes a connector for connecting the user interface to a gas delivery conduit. The connector can comprise an elbow connector which has a non-aligned inlet and outlet. The cushion is typically of a softer, more flexible material such as silicone, that to some extent moulds to the shape of the user's face.

The seal formed between the interface and user's respiratory system allows the mask pressure to be regulated by reducing gas leaks and providing a controlled breathing gases exhaust. Gases may be exhausted from the user interface directly to the surrounding atmosphere through outlet vents or to another component in the breathing assistance system responsible for controlling the exhaust of breathing gas.

Non-sealing user interfaces, particularly nasal cannula, are often employed for supplemental oxygen therapy or other respiratory gases such as Heliox. Typical supplemental oxygen therapy interfaces deliver flow rates of supplementary oxygen of up to 5 l/min directly to the user's nares. Air from the user's surroundings is entrained with the oxygen during normal inhalation, the gases combining to deliver a gas mixture with elevated oxygen concentrations to the user's lungs.

Facial masks are traditionally used for high flow oxygen therapy. Non-sealing nasal high flow (NHF) nasal cannula, such as Fisher & Paykel Healthcare Limited's Optiflow™ Nasal Cannula can be used for flow rate based treatments (including high-flow oxygen therapy). In NHF therapy, the total gas flow is typically up to around 60 l/min.

Direct delivery of breathing gases to a user's nares can be advantageous as the gases can be administered at a greater temperature and humidity than is viable with facial masks.

Our earlier application WO2011078703 discloses a user interface which combines a full face or nasal mask having a sealing cushion, with a nasal cannula which is contained within the mask body. The user interfaces in that application were directed to the problem, amongst others, of flushing the user's dead space.

SUMMARY OF THE DISCLOSURE

It is an object of the present disclosure to provide a respiratory user interface that can improve flushing of a user's anatomical and/or interface dead space, and/or provide a respiratory user interface that can be used for both NHF and NIV therapy, and/or that will at least provide the public or the medical profession with a useful choice.

Accordingly in one aspect the disclosure may broadly be said to consist in a user interface comprising:
 a. a mask body;
 b. a sealing cushion connected to the mask body and configured to seal around a patient's nose and/or mouth; wherein the mask body and sealing cushion together define an interior chamber of the user interface;
 c. a breathing gas delivery inlet provided in the mask body and configured to receive a breathing gas flow from a gas source;
 d. at least one non-sealing nasal prong in the interior chamber;
 e. the user interface further comprising a breathing gas flow director configured to split the breathing gas flow into two flow paths, such that a portion of the breathing gas flow is delivered along a first flow path from the inlet into the interior chamber to pressurise the interior chamber, and such that a portion of the breathing gas flow is delivered along a second flow path from the inlet through the nasal prong.

The flow director may be located upstream of the nasal prong.

The flow director may comprise a flow duct which extends through the interior chamber to the nasal prong, the first flow path being through the flow duct, the flow duct comprising at least one vent aperture which opens into the interior chamber, the second flow path being through the vent aperture. There may be a plurality of vent apertures, and these may be arranged in an array. The or each vent aperture may be located distal from the nasal prong.

The flow director comprises a coupling configured to fluidly couple the flow director to the user interface. The coupling may be configured to couple the flow director to the inlet.

The inlet may be configured to be connected to a conduit connector, the conduit connector being configured to be connected to a gas delivery conduit, the coupling of the flow director being configured to couple with the conduit connector. The conduit connector may be an elbow connector. The user interface may be configured to allow relative rotation between the conduit connector and the flow director. The coupling may be configured to form an interference fit between the flow director and the user interface. The coupling may comprise a snap-fit between the flow director and the user interface.

The flow duct may be configured to define a non-linear flow path to the nasal prong. At least a portion of the flow duct may be serpentine. A part of the flow duct distal from the nasal cannula may be of greater transverse cross sectional area than another part of the flow duct. An intermediate part of the flow duct may be of relatively narrow transverse cross sectional area.

The flow duct may be flexible. The shape and/or length of the flow duct may be adjusted.

The mask inlet comprises a longitudinal inlet axis, the vent aperture in the gas flow director also comprising a longitudinal axis, wherein the axes are substantially parallel.

The mask inlet preferably directs gas into the mask body such that a substantial part of the gas flow has a predetermined gas flow direction, the vent aperture being configured such that gas flow along the second gas flow path is substantially parallel with the predetermined gas flow direction.

The user interface may further comprise at least one vent outlet configured to vent gas from the mask to atmosphere. The vent outlet may be provided in the mask body. The vent outlet may comprise a plurality of mask vent outlets which may be arranged in an array. The vent outlet may be provided on a forward part of the mask body, above the inlet. The vent outlet may provided on a side part of the mask body, to one side of the inlet.

The nasal prong may comprise part of a nasal prong assembly mounted in the mask body, the nasal prong assembly comprising a manifold from which the nasal prong projects, and at least one laterally extending arm which extends from the manifold through the interior chamber such that a distal end of the arm projects externally of the mask body, the distal end comprising, or being provided with, the vent outlet, the arm defining a vent passage through a portion of the arm, the vent passage being in fluid communication with the interior chamber and the vent outlet.

A pair of opposed, laterally extending arms may be provided, wherein each arm is provided with a respective vent passage and vent outlet.

Each vent outlet may comprise part of an arm vent assembly, the arm vent assembly comprising the vent outlet and the vent outlet passage, the arm vent assembly being attached to the distal end of the laterally extending atm.

The arm vent assembly may be attached to the distal end of the laterally extending arm via any one or more of:
a. an interference fit;
b. a snap-fit;
c. overmoulding;
d. co-moulding the arm vent assembly and the arm(s).

The or each vent outlet may project through the sealing cushion.

The vent outlet may be oriented so as to direct vented gases away from the face of the patient. The vent outlet may be oriented to direct vented gases upwardly and/or forwardly with respect to the orientation of the user interface in normal use.

The vent passage may comprise a vent inlet, configured to be exposed to gases in the interior of the vent body, the vent inlet being spaced from the vent outlet, wherein the vent inlet is positioned part way along the arm, distal from both the vent outlet and the nasal prong.

The vent passage may comprise a vent inlet, configured to be exposed to gases in the interior of the vent body, the vent inlet being spaced from the vent outlet, wherein the vent inlet is positioned on the arm, distal from the vent outlet but adjacent the nasal prong.

The vent inlet may be provided on or adjacent the manifold.

The vent inlet may comprise an arcuate slit.

The flow duct of the flow director may comprise a single duct that is in fluid communication with the manifold. The flow duct of the flow director may be bifurcated so as comprise a pair of ducts each in fluid communication with the manifold.

The mask cushion may comprise a face contacting portion and at least one thin or compliant region at least partially within the face contacting portion, wherein the thin or compliant region is adapted to accommodate the placement of a tube between the face contacting portion and a face of a user. The at least one thin region may be adapted to conform to a shape of the tube while substantially maintaining an adequate seal with the face of the user. The least one thin region may be located on a lateral side of the face contacting portion. The at least one thin region may comprise a thin region on each lateral side of the face contacting portion.

According to another aspect of the disclosure there is provided a user interface comprising:
a. a mask body and a sealing cushion connected to the mask body and configured to seal around a patient's nose and/or mouth; wherein the mask body and sealing cushion together define an interior chamber of the user interface;
b. a breathing gas delivery inlet configured to receive a breathing gas flow from a gas source;
c. wherein the user interface also comprises at least one laterally extending arm which extends from the interior chamber such that a distal end of the arm projects externally of the mask body, the distal end comprising a vent outlet, the arm defining a vent passage through a portion of the arm, the vent passage being in fluid communication with the interior chamber and the vent outlet.

The user interface may comprise a nasal seal portion configured to seal around the underside of the nose of the user.

A pair of nasal pillows may be provided and configured to be received in, and seal against, respective nares of the user.

Each nasal pillow may be associated with a respective nasal prong which extends into the nasal pillow. Each nasal prong preferably does not project beyond the respective nasal pillow. For example, the distal end of each prong, and the prong opening, is contained wholly inside the pillow, so as to not to project through the aperture of the pillow.

The user interface may comprise a full face mask configured to seal around both the mouth and nose of the patient. A single seal opening may be provided, exposed to the interior chamber, and configured to seal around the user's mouth and nose. In some cases the interface may comprise a nasal seal opening configured to seal around the underside of the nose of the user, and a mouth seal opening configured to seal around the user's mouth, both the nasal and mouth seal openings being exposed to the interior chamber.

According to a further aspect of the disclosure there is provided a respiratory therapy system comprising the user interface of any one of the preceding statements.

The respiratory therapy system may further comprise any one or more of:

a. a breathing gas flow generator;
b. a breathing gas humidifier; and/or
c. a gas delivery conduit, which may or may not be heated.

Further aspects of the invention, which should be considered in all its novel aspects, will become apparent from the following description.

DESCRIPTION OF THE DRAWINGS

A number of embodiments of the invention will now be described by way of example with reference to the drawings in which:

FIGS. 15a to 15d are further views of the gas flow director of FIG. 12.

DETAILED DESCRIPTION OF SPECIFIC EMBODIMENTS

Figure 1:
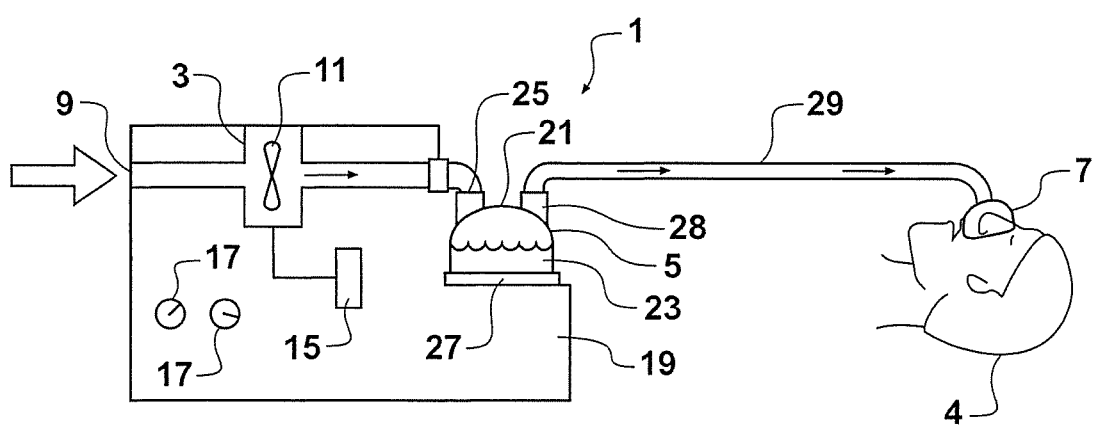
FIG. 1 is a schematic representation of a respiratory system configured to supply pressurised and humidified breathing gases to user through a user interface.

An example respiratory therapy system suitable for supplying breathing gases to user U is illustrated in FIG. 1. The example respiratory therapy system 1 comprises a gas source 3, a separate humidifier 5, and a user interface 7.

The gas source 3 provides a supply of breathing gas to the humidifier 5. The gas source could comprise a source of supplementary breathing gas such as pressurised supplementary oxygen, as might be provided in a hospital environment for example. The gas source may alternatively or additionally comprise a blower in which breathing gas, being ambient air, is drawn into the gas source 3 through an inlet 9 in the gas source casing by an impeller 11. The rotational speed of the impeller 11 is modulated to regulate the quantity of air drawn into the gas source 3 and the supply of breathing gas to the respiratory therapy system.

By breathing gas we include any single gas or multiple gases that are breathable by a user of the system 1.

The pressure and/or flow rate of breathing gas exiting the gas source 3 is regulated by a controller 15. The controller 15 manipulates the rotational speed of the impeller 11 according to one or more predetermined algorithms and in accordance with one or more user inputs provided via a user input 17.

The illustrated gas source 3 represents an actively controlled flow generator similar to a hospital compressed air system or a ventilator or home CPAP unit (such as Icon™ or the SleepStyle™ series produced by the Fisher & Paykel Healthcare). Other gas sources, such as a compressed oxygen cylinder with suitable pressure or flow regulation, may also be used to supply breathing gas.

The outlet of the gas source 3 may be coupled to a separate humidifier 5. The humidifier 5 heats and humidifies the breathing gas prior to delivery to a user 1. The humidifier may be integrated with the gas supply.

The humidifier 5 comprises a base 19 and a humidifier chamber 21. The chamber 21 is configured to hold humidification fluid, such as water, 23 and may be able to be disengaged from the humidifier base 19 to allow it to be filled or replaced. The humidifier 5 receives gases from the gas source 3 through chamber inlet 25.

The humidifier base 19 can include a heater such as a heater plate 27. The chamber 21 rests on the heater plate 27 when engaged with the humidifier base 19. The heater plate 27 dissipates heat, generated by electrical resistance, to the chamber 21. The water chamber 21 preferably has a heat conductive base to enable the heat generated by the heater plate 27 to pass efficiently to the humidification fluid 23.

Controller 15 can also control the humidifier 5, and in particular the supply of electrical energy to the heater plate 27 to regulate the temperature and humidity of the breathing gas supplied to the user.

The breathing gas is supplied to the user U via a chamber outlet 28 and a breathing gas delivery conduit 29 which may incorporate a heater wire to heat the breathing gases during transportation to the user interface 7. The electrical energy supplied to the heater wire may be controlled by controller 15.

The controller 15 may receive feedback from one or more sensors incorporated in a control network throughout the respiratory therapy system to monitor properties of the breathing gas, such as pressure, flow, temperature and/or humidity.

The user interface 7 couples the user U with the respiratory therapy system 1, delivering heated and humidified gases from the humidifier 5 to the user's respiratory system. The illustrated user interface U comprises a full face mask arranged about a nasal cannula. The nasal cannula is enclosed between the user's face and the mask. References in this specification to a user interface include a user interface comprising a full face mask covering the mouth and nose of the user, and to a user interface comprising a nasal mask covering only the nose of the user.

The cannula comprises a pair of nasal prongs that project into the user's nares. The prongs preferably have a wide bore to permit high breathing gas flow rates (ideally, capable of delivering enough breathing gas for peak inspiratory demand with the lowest flow resistance), but are non-sealing prongs that do not seal with the user's nostrils. The prongs are preferably configured, in particular the bore of the prongs, to be able to deliver a total gas flow of up to about 60 l/min.

It is preferable that flow through the cannula is continuous and unidirectional to constantly flush both mask and anatomical dead spaces of expired gases. Re-inhalation of expired CO2 can be reduced by continuous purging of the user's nares with fresh gas having oxygen concentrations at or above atmospheric air (the oxygen concentrations would be above that of atmospheric air if supplemental oxygen has been added to the flow path) forcing expired gases through the space about the nasal prongs. The expired gases are evacuated subsequently from the user interface 2 through an exhaust in the form of a vent located in the mask body.

Preferably, breathing gases are delivered at a flow rate exceeding the user's peak inspiratory flow requirements to ensure that expired gases are purged throughout the entire respiratory cycle.

The delivery and exhaust of gases to and from the mask respectively may be controlled to regulate the pressure within the mask. Exhaust gas flow rates may be regulated actively by a component within the breathing assistance system (such as the gas supply device) or passively (by fixing the restriction to gas flow through variable or non-variable outlet vents). A combination of active and passive exhausting may be implemented alternatively.

In these ways, airway pressure experienced by a user can be regulated by manipulating the gas delivery flow rate supplied to the nasal cannula and the outlet flow rate exhausted from the mask.

A Positive End Expiratory Pressure (PEEP) can keep the airways and alveoli from collapsing at the end of expiration and also serve to reopen airways and alveoli that have already collapsed.

The therapeutic provision, PEEP, can improve gas exchange (by way of decreased intra pulmonary shunt), reduce the resistance to airflow (by reducing flow resistance within the lungs), and make the lungs less stiff (increased lung compliance). Levels of oxygen and carbon dioxide also may improve, reducing the need for supplemental oxygen and the sensation of breathlessness by the patient.

PEEP may also improve cardiac performance by increasing mean intra thoracic pressure. PEEP is of special advantage to assisting in the treatment of obstructive lung diseases and heart failure, including emphysema, bronchiectasis, chronic bronchitis, cystic fibrosis and pulmonary edema.

Additionally, breathing gases can be delivered to the user at, or near, optimal temperature and humidity (warmed and fully saturated with water vapour at body temperature −37° C., 44 mg/L humidity) as the gases are delivered predominantly to the user's nares. Subjects (patients) can tolerate greater gas temperatures and humidity when the gases are delivered to the nares than is viable when administered by facial mask. Emulating the conditions within healthy adult lungs (37° C., 44 mg/L humidity) can help maintain healthy mucociliary function in users with respiratory disorders affecting secretion.

The user interface 7 can therefore administer a broad range of treatments viably (including PAP and humidity therapy), as it combines the advantages of a sealing user interface (expiratory pressure regulation) and a high flow nasal interface (dead space flushing and optimal humidity delivery). The user interface 7 is configured to provide the different treatments at the same time, or to providing a combination of treatments, or to provide a hybrid therapy, without requiring the user interface 7 to be removed from the user's head and replaced.

"Dead space" as used here refers to both apparatus dead space and anatomical dead space. Apparatus dead space refers to zones in any additional equipment such as mask and circuits where the expired gas can be re-breathed again. Anatomical dead space includes areas in the nose, pharynx, trachea and bronchi where CO2 levels can build up. The high flow nasal interface can provide improved flushing of the anatomical dead space.

Several embodiments of user interface 7 are described in detail below.

Figure 2:
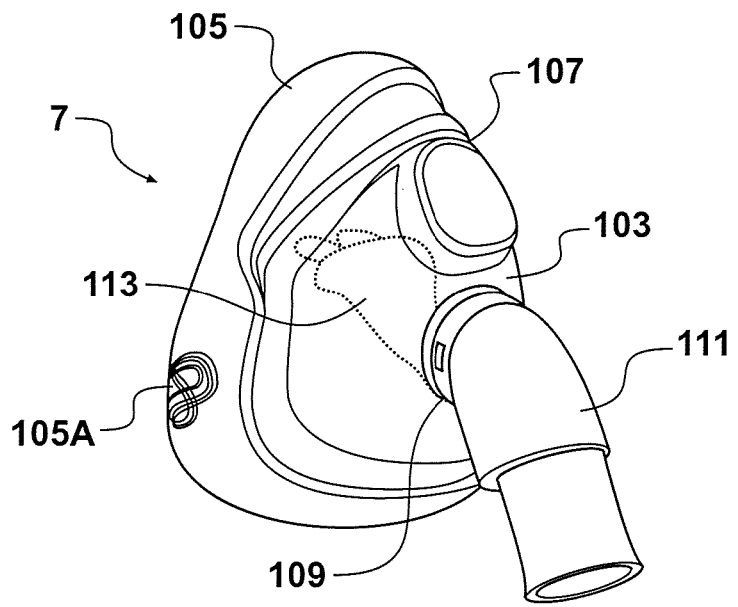
FIG. 2 is a perspective view of a respiratory user interface in accordance with the present disclosure.

With reference to FIG. 2, a user interface 7 comprises, in this example, a full face mask comprising a rigid or semi-rigid mask body 103 to which a relatively soft and flexible mask cushion 105 is attached, preferably by overmoulding 107. The mask cushion 105 is configured, by a combination of shape and material selection, to form a seal with the user's face in use, to resist pressurised gas in the user interface 7 from leaking between the cushion 105 and the user's face. The mask body 103 is provided with a breathing gas inlet 109 in the form of a circular inlet aperture. The aperture could be any other desired shape, including oval for example.

NIV masks commonly are used on patients who also require a nasogastric (NG) tube, a nasojejunal (NJ) tube and/or an oro-gastric (OG) tube for feeding or delivery of medication. Traditionally, NIV masks are not designed for use in combination with an NG, NJ and/or OG tube and, as such, the efficacy of the NIV therapy can be compromised when such a combination is desired.

Certain features, aspects and advantages of the present embodiments can reduce the gaps that form between the mask cushion 105 and the surface of the user's face when a conduit such as an NG tube 54 is used by providing a conformable or compliant region 105A in the mask cushion 105 that can conform to the NG tube to a degree sufficient to create or maintain an adequate seal with the user's face.

The conformable or compliant region 105A can be of any suitable arrangement to increase the conformability or compliance of a portion of the cushion 105 relative to adjacent or surrounding portions of the cushion 105. As described herein, the conformable or compliant region 105A can be or comprise a region of thinned material or a region of different material, among other possible arrangements. The conformable or compliant region 105A creates a tube path that is more compliant and flexible than the surrounding or adjacent portions of the cushion 105.

In some configurations, the conformable or compliant region 105A is more compliant and flexible than any other portion of the cushion 105. The conformable or compliant region 105A can stretch and deform around the tube, which results in smaller gaps at the side of the tube than a cushion not having the specially configured tube paths. The size of the gaps will be largely dependent on the tube size that is being used. The mask cushion 105 may not lift away from the face to accommodate the tube to the same degree as a traditional mask cushion that does not include tube paths.

As described above, the conformable or compliant region 105A can be of any suitable arrangement that provides for conformance to the type or size of the tube or tubes intended for use with the user interface 7. In some configurations, the conformable or compliant region 105A is substantially more conformable or compliant than surrounding or adjacent portions of the cushion 105. In some configurations, the increased conformability or compliance is at least partially the result of using a different material in the conformable or compliant region 105A relative to surrounding or adjacent portions of the cushion 105. For example, the increased conformability or compliance can be achieved through the localized use of a more elastic and flexible material. The different material can have a higher elasticity or different modulus of elasticity compared to the material of surrounding or adjacent regions of the cushion 105. Materials can include a different grade of silicone that is less hard or a more flexible TPE, for example but without limitation. In some configurations, the different material can also have a different thickness (e.g., less thickness) compared to the material of surrounding or adjacent regions of the cushion 105. The different material can be coupled to the material of surrounding or adjacent regions of the cushion 105 by any suitable process, which can include adhesive or chemical bonding or a co-molding or over-molding process, for example and without limitation, or any other appropriate method. In arrangements in which different material is utilized for the conformable or compliant region 105A, the different material can extend beyond the conformable or compliant region 105A. For example, such an arrangement can provide a greater surface area overlap for bonding of the two materials to one another.

In this example a connector, being an elbow connector 111, is fluidly coupled to the inlet 109 such that breathing gas can enter the interior of the mask body 103 via the elbow connector 111. The coupling between the mask body 103 and the elbow connector 111 may incorporate a rotatable or swivel coupling allowing relative rotation between the mask body 103 and the elbow connector.

Figure 3:
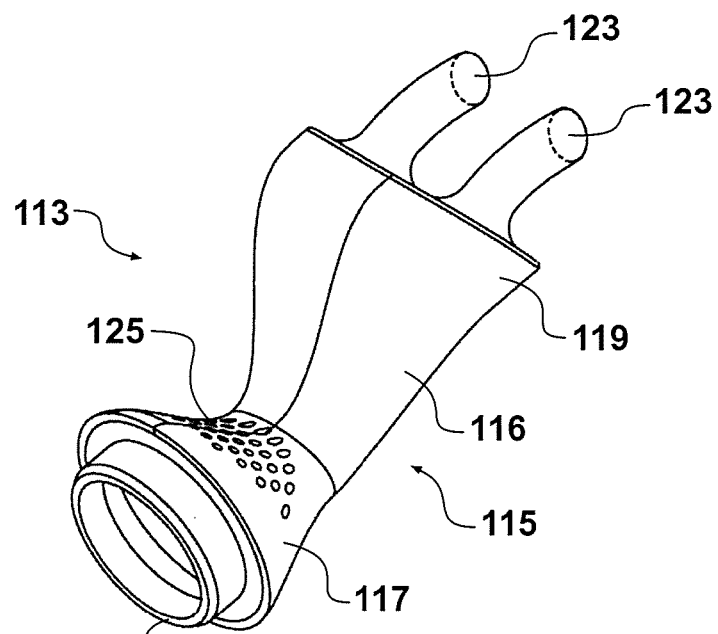
FIG. 3 is an enlarged perspective view of a gas flow director and nasal cannula comprising part of the user interface of FIG. 2.
Figures 4A, 4B:
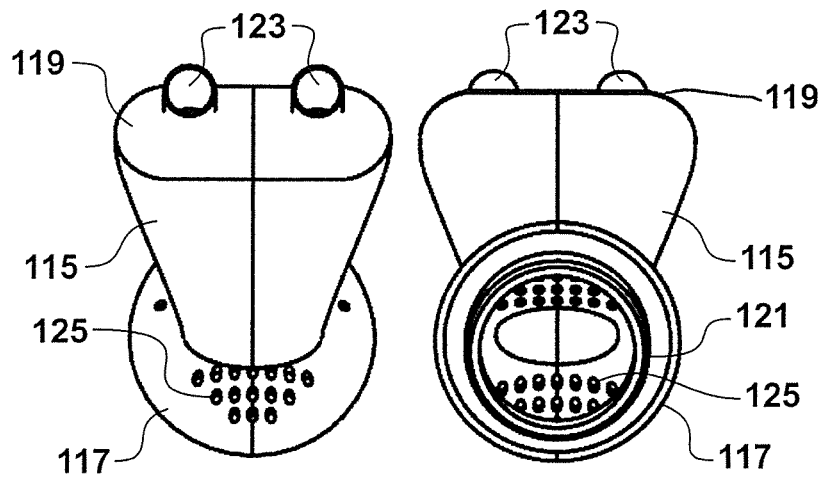
FIGS. 4a to 4d are further views of the gas flow director of FIG. 3.
Figures 4C, 4D:
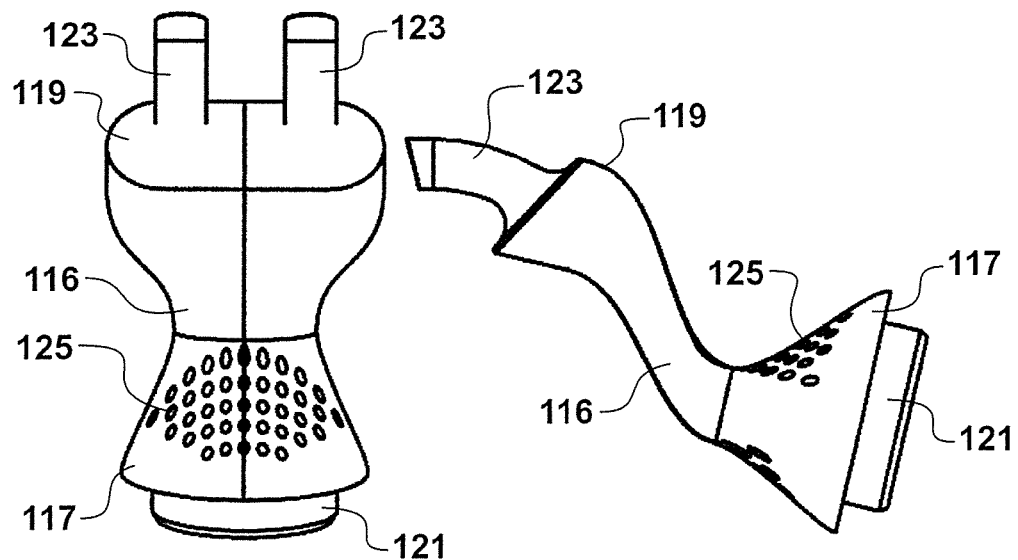

With additional reference to FIGS. 2 and 3, a breathing gas flow director and nasal cannula assembly 113 is mounted inside the user interface 101 in the interior space or chamber defined by the mask body 103 and mask cushion 105. The assembly 113 comprises an elongate duct 115 of serpentine form comprising a relatively narrow diameter middle or waist region 116, which flares radially outwardly to define a wider diameter breathing gas inlet end 117 and a wider diameter breathing gas outlet end 119.

The inlet end 117 comprises a coupling 121 configured to couple the inlet end 117 to a mask coupling 122 of the mask body 103, and in particular to the inlet 109. The mask body 103 may be provided with a suitable coupling formation configured to engage with and retain the coupling 121 in the desired position within the mask body 103. The coupling 121 could form an interference or friction fit with the mask body 103, or could comprise a positive engagement mechanism, such as a snap-fit type mechanism, for example.

The outlet end 119 terminates in a nasal cannula comprising a pair of non-sealing nasal prongs 123 which project from the outlet end 119 and are shaped and dimensioned to be received in a user's nares, but not to seal with the nares. Thus the prongs 123 are configured such that a gas leak path is defined around the prongs 123 when inserted into the user's nares.

The assembly 113 further comprises at least one vent aperture (which may be referred to as a supplementary vent or flow aperture) and in this example, an array of a plurality of vent apertures 125. The vent apertures 125 in this example are provided on the outwardly flared inlet end 117 of duct 115, and comprise a first array on an upper part of the inlet end 117, and a second array on a lower part of the inlet end 117.

Figure 5A:
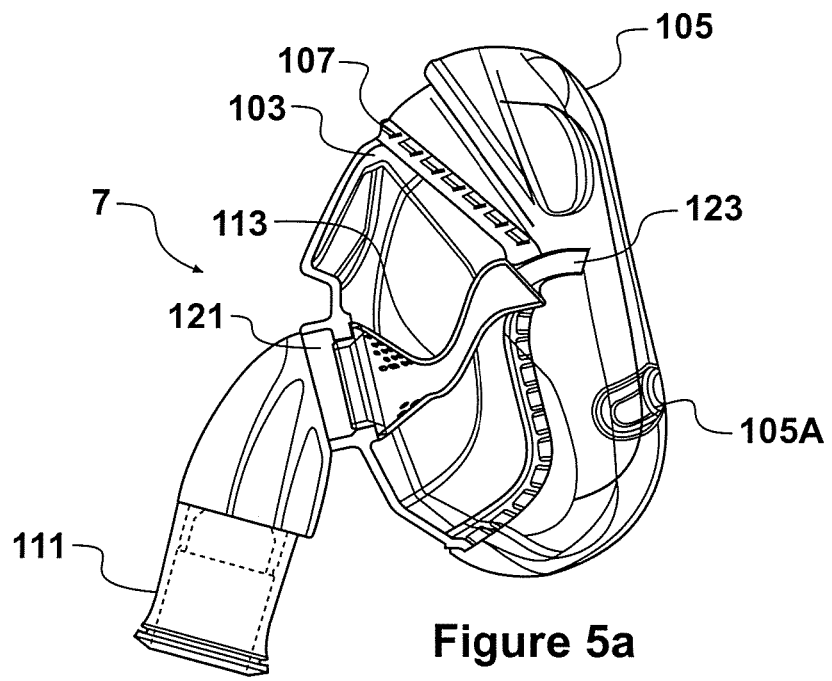
FIGS. 5a and 5b are sectional side views of the user interface of FIG. 2.
Figure 5B:
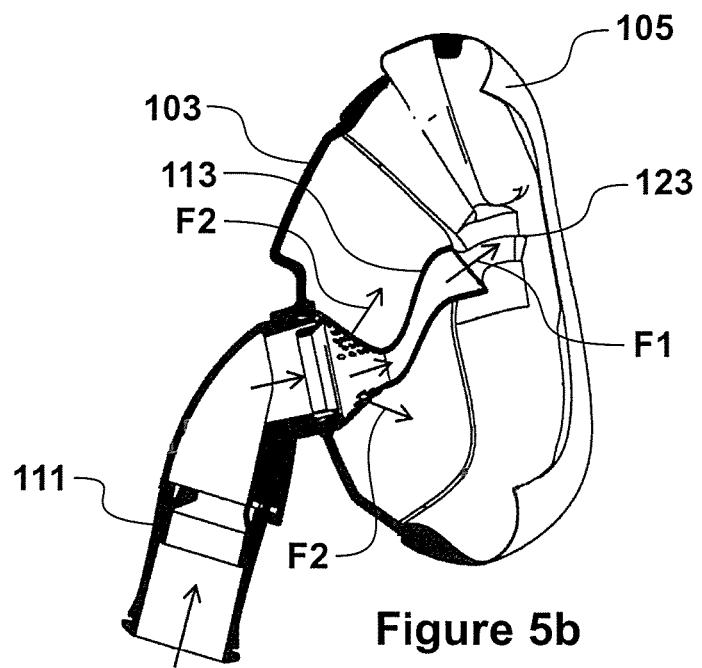

The inlet end 117, the outlet end 119 and nasal prongs 123, and the vent apertures 125, together provide two breathing or inspiratory gas flow paths along which breathing gas can flow from the user interface inlet 109. The first flow path F1, with reference to FIG. 5, is from the inlet end 117 to the nasal prongs 123 to deliver breathing gas directly to the nares of the user. The second gas flow path F2 is from the inlet end 117 to the vent apertures 125 to deliver breathing gas to the interior space or chamber defined by the mask body 103 and mask cushion 105. The first flow path F1 therefore delivers breathing gases directly to the user's nares, whilst the second flow path F2 pressurises the interior of the user interface 7. The first flow path F1 assists in flushing dead space of the user, whilst the second flow path F2 delivers pressurised therapy. The second flow path F2 can also assist in forming a good seal between the cushion 105 and the user's face. The assembly 113 thus functions as a breathing gas flow splitter which generates a plurality of different output flow paths from a single inlet flow source.

Referring in particular to FIG. 5, breathing gas is directed to the mask inlet 107 at a pressure P1 and a flow rate F1, where it is divided into two flow paths F2, F3 the first having a pressure P2 and flow F2, and the second having a pressure P3 and flow F3. A portion of the breathing gas flows through the vent apertures 125, into the interior of the user interface 101, and a portion of the breathing gas flows through the cannula to the nasal prongs 123. Diversion of the breathing gas allows the user interface 7 to provide the pressure support of NIV via the mask body 103 and cushion 105, and the high flow flushing of nasal high flow therapy via the cannula. Preferably, P2>P3 and F3>F2. The flow through the cannula has a relatively high flow rate and relatively low pressure, and the flow in the mask body 103 has a relatively high pressure and relatively low flow rate.

Figure 6:
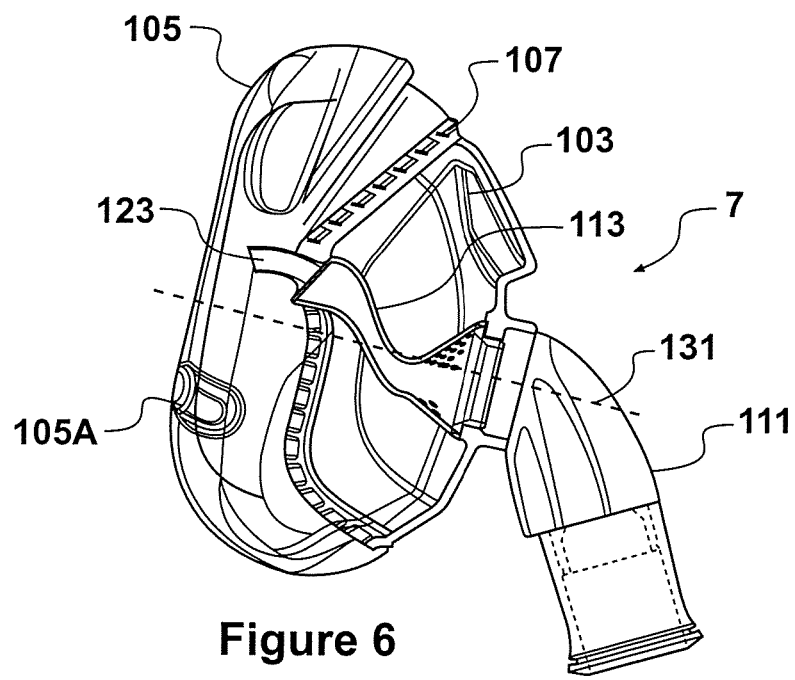
FIG. 6 is a further sectional side view of the user interface of FIG. 2.
Figure 7:
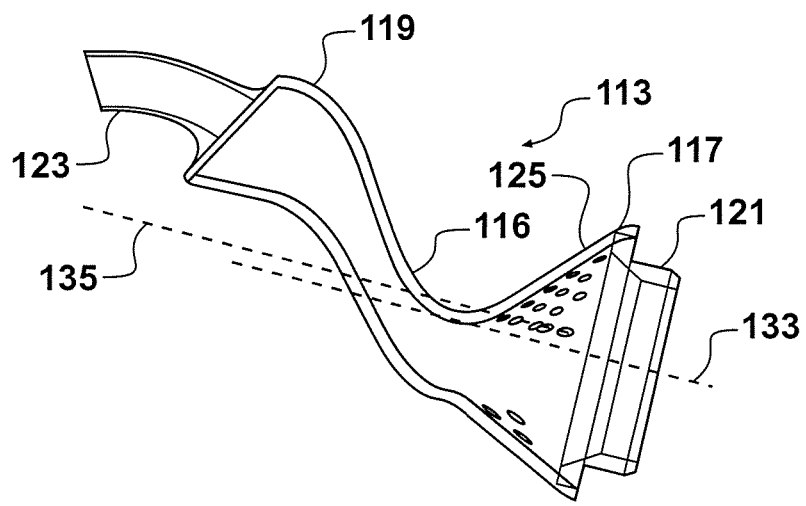
FIG. 7 is a sectional side view of the gas flow director of FIGS. 3 and 4.
Figure 8:
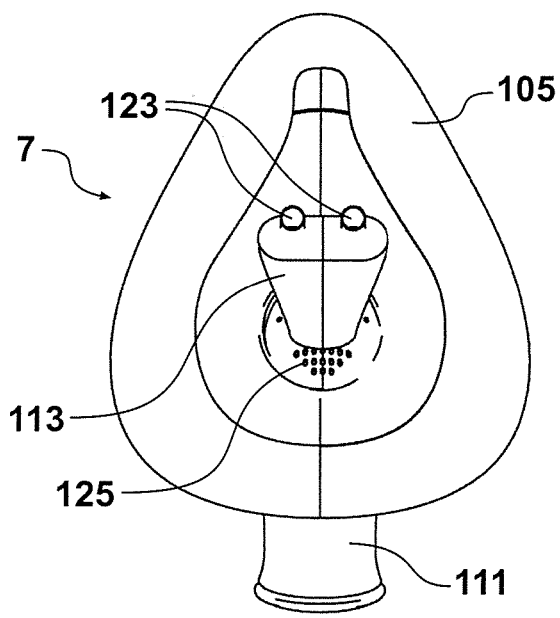
FIG. 8 is a rear view of the user interface of FIG. 2.
Figure 9:
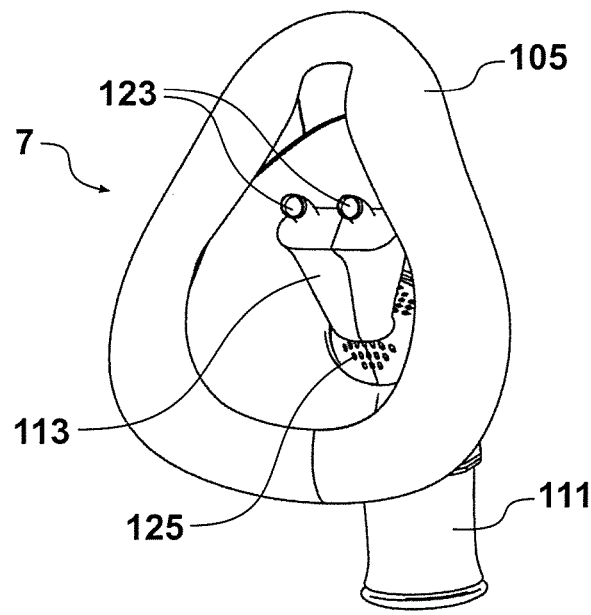
FIG. 9 is a perspective view of the user interface of FIG. 2.

Referring additionally to FIGS. 6 and 7, the patient interface 7 defines a notional interface inlet axis 131 which extends through the centre of the inlet 109, the inlet 109 being of tubular form which projects from the front of the mask body 103. In this example the interface inlet axis 131 is equivalent to an axis of a cylinder representative of the interface inlet 109. The flow director assembly 113 defines a notional coupling axis 133 which extends through the centre of the coupling 121, the coupling 121 also being of tubular form in this example, projecting from the inlet end 117. Further, each vent aperture 125 defines a notional vent axis 135 which extends through the centre of each vent aperture 125. The relationship between, and in particular the relative orientation of, these axes can help to achieved one or more desired characteristics of the breathing gas flow. The coupling axis 133 is substantially parallel with the inlet axis 131, and in this example, these axes are concentric and aligned so as to effectively define a common axis. The vent axis 135 is parallel with the inlet axis 131 and/or the coupling axis 133. In the illustrated configuration, the inlet axis 131, coupling axis 133 and vent axis 135 are parallel. The relative alignment and relationship between these axes can assist in reducing the pressure drop of breathing gas passing through the vent hole arrangement into the mask body 103 as it minimizes direction change of the flow. The mask coupling 121 of the assembly 113 couples to the mask inlet 109 along the inlet axis 131 and coupling axis 133.

With reference to FIG. 10 two user interface vent arrangements are shown. Typically, NIV masks do not require mask vent arrangements, as they have auxiliary vent arrangements (for single limb systems), or an expiratory limb of the ventilator allows the removal of breathing gas during exhalation. When incorporating NHF therapy however, to allow flushing of the user's dead space, a mask vent arrangement can be beneficial in ensuring fresh breathing gas is supplied via the cannula assembly 113. This is because as the NHF therapy is supplied, a constant vent from the user interface 101 allows used gas formerly in the user's dead space to be vented and replaced with fresh breathing gas. The vent in the mask body is therefore beneficial in that it allows for constant nasal flushing so as to relatively quickly dissipate carbon dioxide before a build-up can occur in the internal chamber of the user interface.

Figures 10A, 10B:
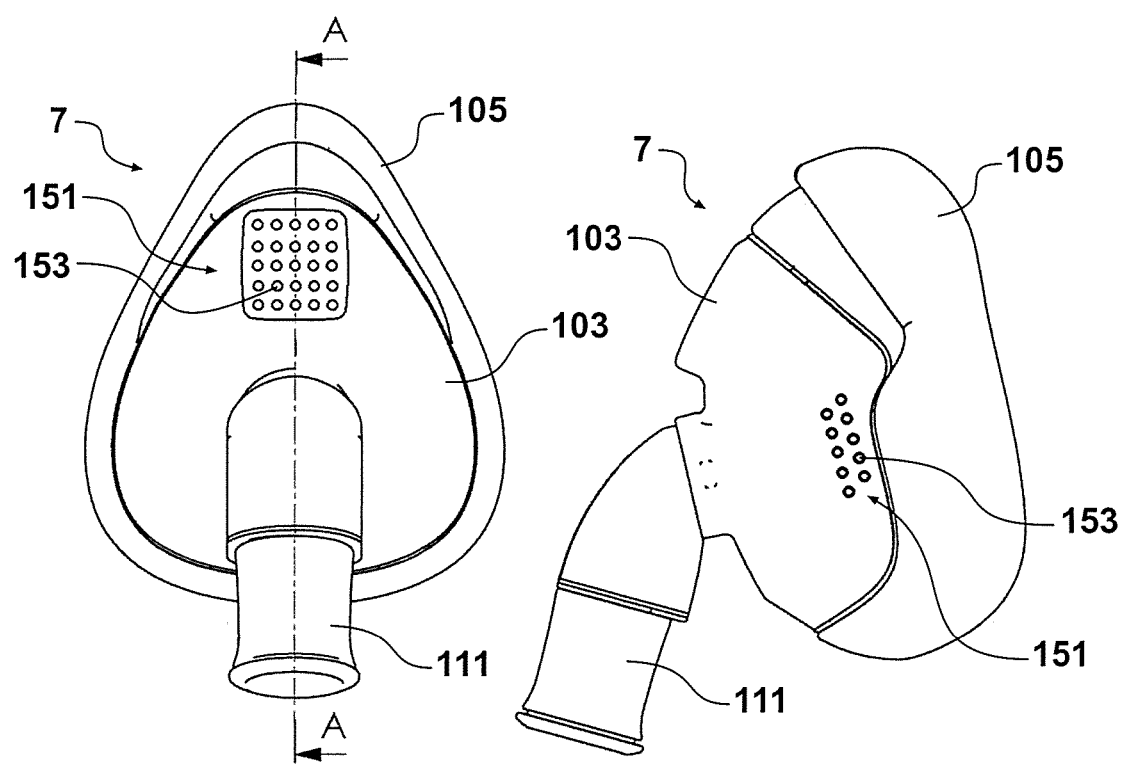
FIGS. 10a and 10b are front and side views of a user interface in accordance with the current disclosure showing different outlet vent configurations.
Figure 11:
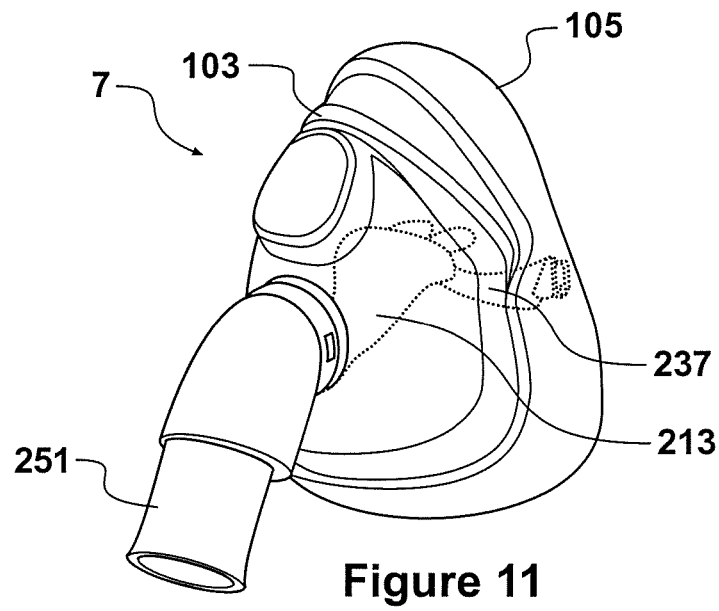
FIG. 11 is a perspective view of another embodiment of a respiratory user interface in accordance with the present disclosure, coupled to an elbow flow connector.
Figure 12:
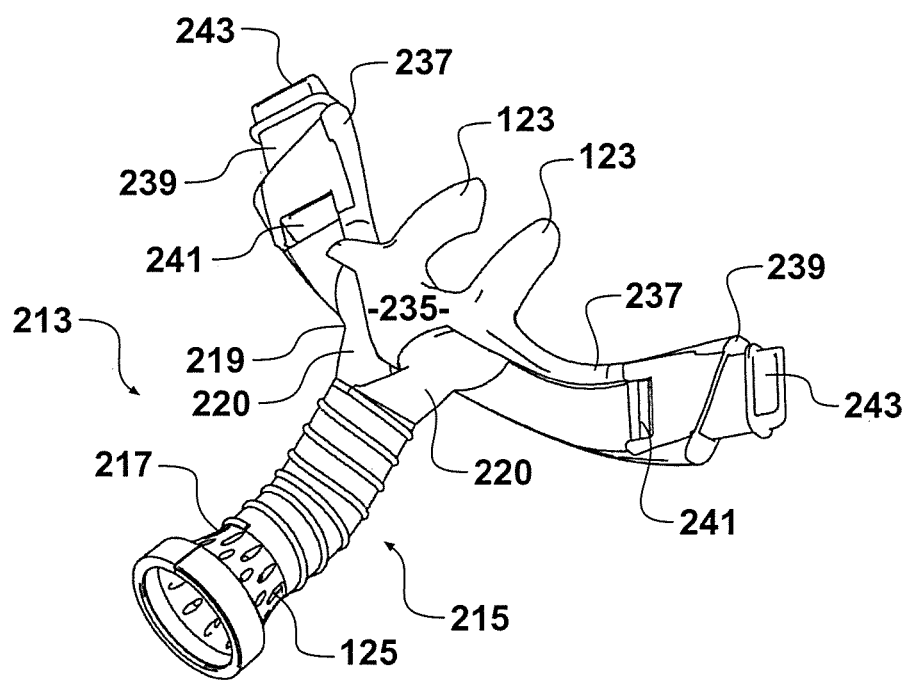
FIG. 12 is an enlarged perspective view of a gas flow director and nasal cannula comprising part of the user interface of FIG. 11.
Figure 13A:
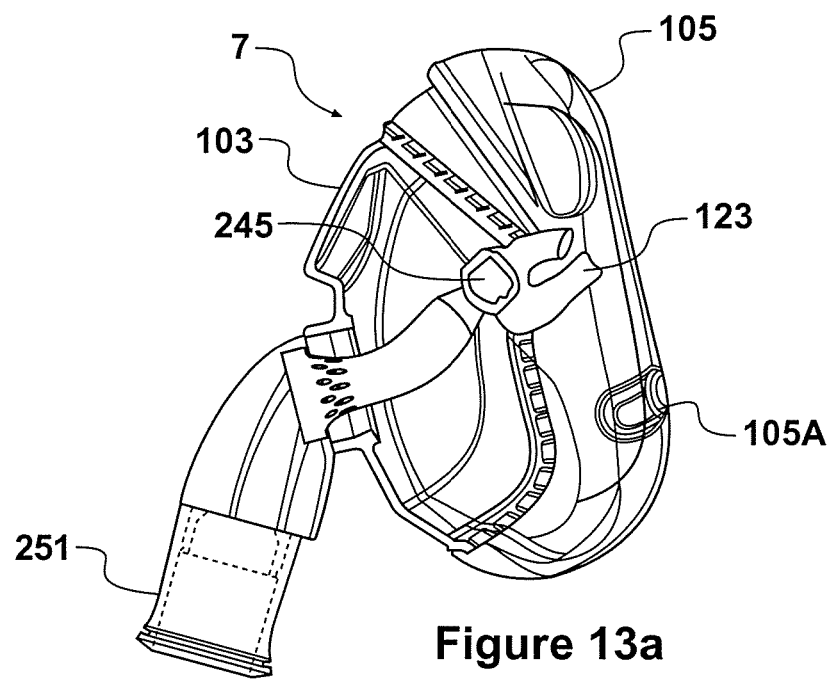
FIGS. 13a and 13b are sectional side views of the user interface of FIG. 11.
Figure 13B:
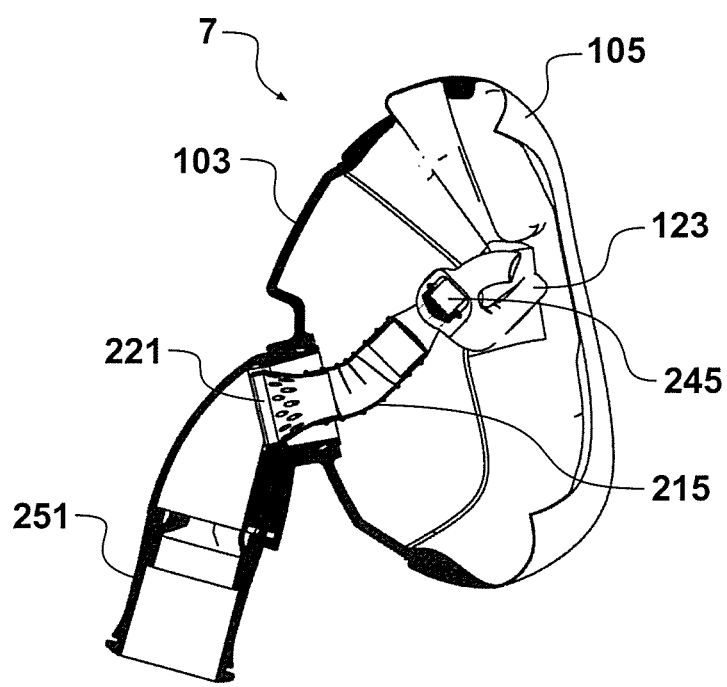

Two embodiments of the user interface 7 with two different possible mask vent arrangements 151 are shown. Each vent arrangement 151 comprises an array of a plurality of vent holes 153. Any number of vent holes 153 can be provided, and in any desired shape and/or size of array. Multiple arrays can be provided. In the example of FIG. 10a, the vent array is provided on the front of the mask body 103, directly above the mask inlet 107. In the example of FIG. 10b, the vent array is provided on the side of the mask body 103. The orientation of vent holes, number, shape, cross sectional area, and/or location of the vent holes 153 can vary.

Referring now to FIGS. 11 to 16, a user interface 7 is shown having many of the features described above. Like features have been given like references. This example uses an alternative flow director and cannula assembly 213. The principles of operation, and the advantages are similar to those provided by assembly 113.

In this example, the assembly 213 comprises an elongate duct 215 of serpentine form comprising a relatively constant diameter flexible tube comprising a breathing gas inlet end 217 and a breathing gas outlet end 219. Duct 215 is adjustable, and this example is length adjustable such that the distance between the inlet end 217 and the outlet end 219 can be varied.

The outlet end 219 of assembly 213 bifurcates into a pair of end tubes 220, each of which is in fluid communication with a respective one of the pair of non-sealing nasal prongs 123.

The assembly 213 further comprises at least one vent aperture and in this example, an array of a plurality of vent apertures 125. These vent apertures 125 in this example are provided on the inlet end 217, and are spaced around the inlet end 217.

The nasal prongs 123 in this example are provided on a central manifold 235 or cannula body from which a pair of opposed, laterally extending arms 237 depend. Each arm 237 extends laterally away from the manifold 235 and the prongs 123 such that a distal end of each arm 237 projects externally through a respective side portion of the user interface 101. In this example, each arm 237 projects through the mask cushion 105, but each arm 237 could project through the mask body 103.

Each arm 237 comprises an atmospheric vent 239 which provides a venting flow path between the interior space or chamber of the user interface 101 and atmosphere, external of the user interface 101. In this example each vent 239 is provided as a vent assembly which plugs into, or is otherwise attached to, the distal end of each arm 237. Each vent assembly comprises a vent inlet 241, and vent outlet 243 and a vent passage 245 through the vent assembly of the arm 237 which is in fluid communication with the vent inlet and outlet 241, 243. Each vent 239 allows gas within the user interface 101 to vent to atmosphere as described above. Further, the provision of the laterally extending arms 237 provides further structural integrity to the flow director and cannula assembly 213, and helps to securely locate and retain that assembly 213 in the desired position and orientation within the user interface 101.

Each vent assembly can be attached to each arm 237 by:
Interference fit;
Overmoulding the arms 237 over the vent assemblies; or
Including the vent assemblies when moulding the assembly 213.

In the illustrated configuration, the arm vent outlet 243 is angled upwards and forwards with respect to a user U of the user interface 101. The arm vent outlet 241 could provide an outlet vent flow path in any other orientation. Orientations that face away from the user U may be beneficial as the user U will not feel the vented gas stream created by the vent 239. However for NIV purposes, this may not be required, if the patient is not conscious. The arm vent outlet 243 may alternatively be angled downwardly/sideways so as that exhaled gases are directed away from the caregiver's face.

The inlet end 217 comprises a coupling 221 configured to couple the inlet end 217 to a mask coupling 222 of the mask body 103, and in particular to the inlet 109. The mask coupling 222 may comprise a suitable coupling formation configured to engage with and retain the coupling 221 in the desired position within the mask body 103. The couplings 221, 222 could form an interference or friction fit with the mask body 103, or could comprise an engagement mechanism, such as a snap-fit type mechanism, for example. In the illustrated embodiment, the couplings 221, 222 are located near the inlet 107 of the user interface 101. To couple the assembly 213 to the user interface 101, coupling 221 is inserted into the coupling 222. An interference fit is formed between the two, retaining the assembly 213 in place.

The user interface 7 is shown connected to an elbow connector 251 which also connects to a gas delivery conduit (not shown) to deliver breathing gas to the user interface 7. Any other type of connector can alternatively be used between the user interface 7 and the gas delivery conduit.

In the illustrated configuration, the elbow connector 251 rotatably connects to the mask inlet 107. The coupling 221 of the assembly 213 couples to an interior surface of the elbow connector 251 near the mask inlet 107. The coupling 221 comprises a slip ring arrangement, wherein the outer surface of the coupling 221 can rotate with respect to the inner surface of the coupling 221. This allows the elbow connector 251 to rotate with respect to the mask body 103 and the assembly 213, whilst the patient interface 7 remains stationary. Breathing gas is again divided into two flow paths by the follow director assembly 213 to facilitate NIV and NHF.

Figure 14:
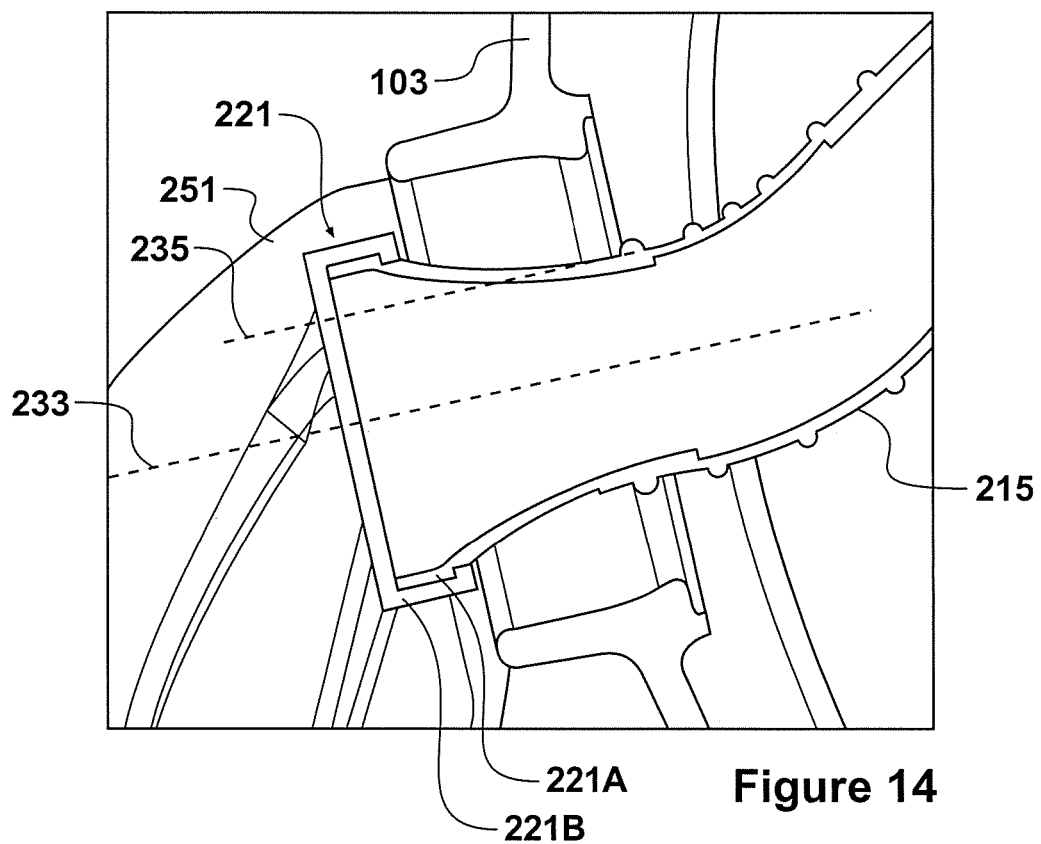
FIG. 14 is an enlarged part sectional side view of part of the user interface of FIG. 11.
Figures 16A, 16B:
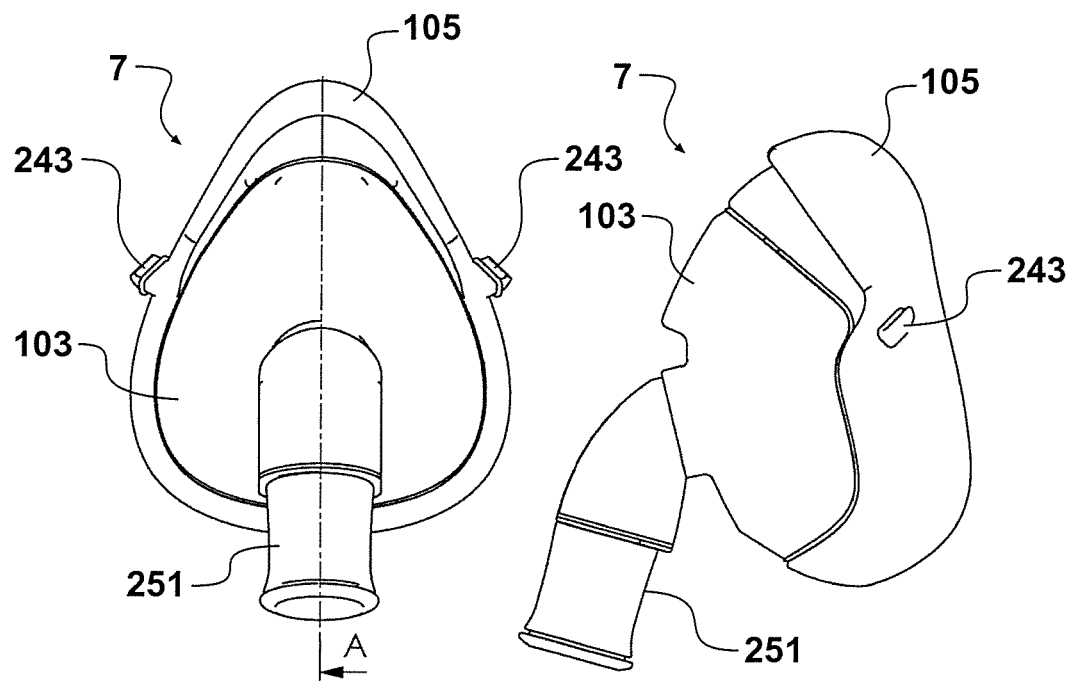
FIGS. 16a to 16d are further views of the user interface of FIG. 11.
Figures 16C, 16D:
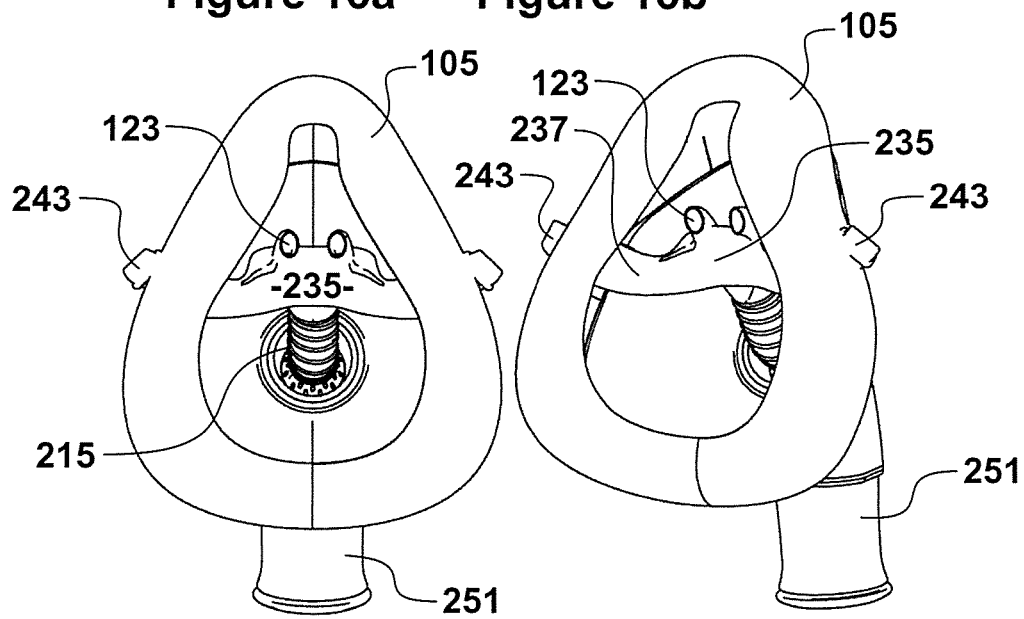
Figure 17:
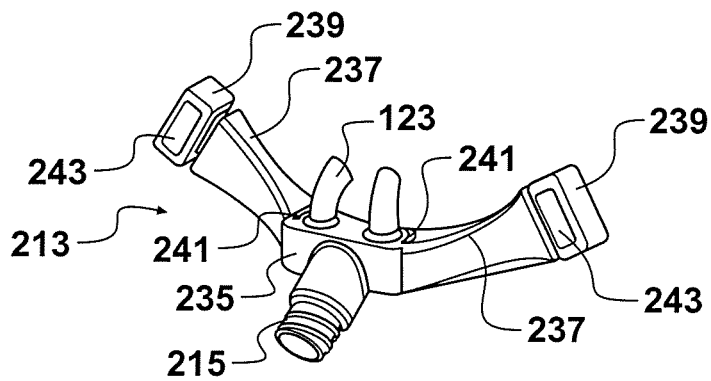
FIG. 17 is a perspective view of another embodiment of a gas flow director and nasal cannula for use with the user interface of FIG. 11.
Figure 18:
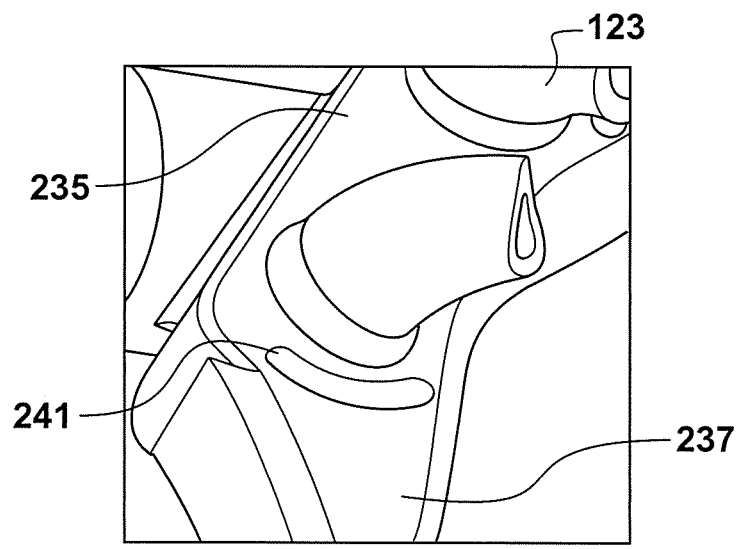
FIG. 18 is an enlarged view of a central part of the flow director of FIG. 17.

With additional reference to FIG. 14, a magnified sagittal cross section of the user interface 7 is shown, focusing on the interaction between the mask inlet 107, coupling 221 and elbow connector 251.

The coupling 221 includes a coupling internal ring 221A and a coupling external ring 221B.

The coupling external ring 221B is configured to form an interference fit with the elbow connector 251 at the mask inlet 107. The coupling internal ring 221A is integrally formed with the assembly 213, and is configured to fit inside the coupling external ring 221B. As the internal and external rings 221A, 221B are not connected, the internal ring 221A can rotate with respect to the external ring 221B. Therefore, as the elbow connector 251 is rotated in use, the external ring 221B is able to rotate with the elbow connector 251, maintaining its interference fit, while the internal ring 221A remains un-rotated. Again the vent axis is parallel to the coupling axis.

In the illustrated configuration, the duct 215 of assembly 213 is a flexible tube. Additionally, the arms 237 are made from a flexible material, such as silicone. The flexible duct, and flexible arms 237 allow the assembly 213 to fit a wide variety of face shapes and sizes.

Referring now to FIGS. 17 to 21, flow director and cannula assembly 213 has been modified to reposition arm vent inlet 241. In particular, the relative position between the vent inlet 241 and the nasal prongs 123 has been changed.

The arm vent inlets 241 of this configuration are located relatively close to the nasal prongs 123, on a proximal surface of the central manifold 235 of the nasal cannula. Locating the arm vent inlet 241 close to the nasal prongs 123 can be beneficial in increasing the efficiency with which the user interface 7 vents breathing gas with a relatively high $CO_2$ concentration, as breathing air exhaled by the user is naturally directed into the arm vent inlets 241.

Each arm vent outlet 243 is included in a vent 239 which is configured as an insert received in the open end of each arm 237. In the illustrated configuration, the vent 239 is a separate component to the cannula arms. The vent 239 can be inserted into the vent channel 245 defined within each arm 237, being secured in place by an interference fit. The cushion 105 of the user interface 7 can be sealingly secured between the vent 239 and the respective arm 237. In an alternate configuration, the assembly 213 can be over-moulded over the vents 239 to form an integrated component. In yet another configuration, the vents 239 can be an integral part of the arms 237 themselves, that is, moulded simultaneously with the arms, from the same material.

Figure 19:
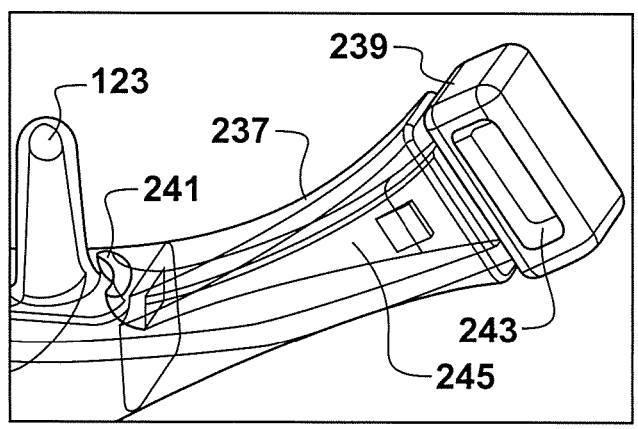
FIG. 19 is an enlarged, part transparent, perspective view of part of the flow director of FIG. 17.
Figure 20:
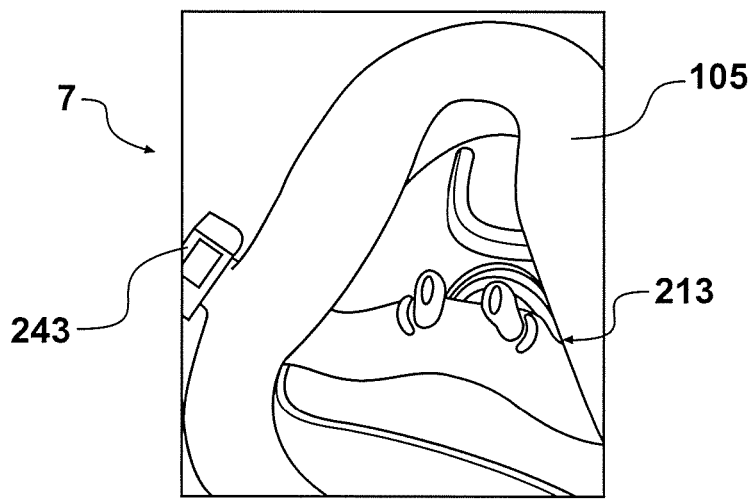
FIG. 20 is a perspective view from the rear of the user interface of FIG. 11 and the gas flow director of FIG. 17.

With particular reference to FIG. 19, the vent channel 245 is largely rectangular in transverse cross section, and extends laterally within the arm 237 from the arm vent inlet 241, continuing through the vent 239, to the arm vent outlet 243. When the interior of the user interface 7 is pressurized, this channel 245 vents breathing gases from inside the user interface 7, allowing fresh breathing gases to be delivered to the user from the gas supply.

In the illustrated configuration, the arm vent inlet 241 is located on the proximal surface of the nasal cannula manifold, close to the nasal prongs 123. In other configurations, this may not necessarily be the case. The arm vent inlet 241 may be spaced further away from the nasal prongs 123, and/or may be on a surface other than the proximal surface (distal surface, upper surface, lower surface etc.).

With reference to FIG. 21 alternate configurations of assembly 213 are shown.

Figure 21A:
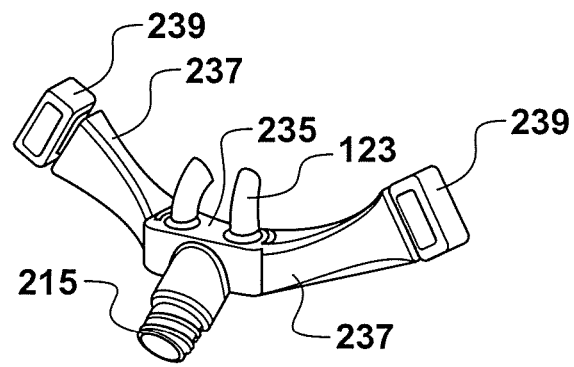
FIGS. 21a and 21b are perspective views of two variants of the flow director of FIG. 17.
Figure 21B:
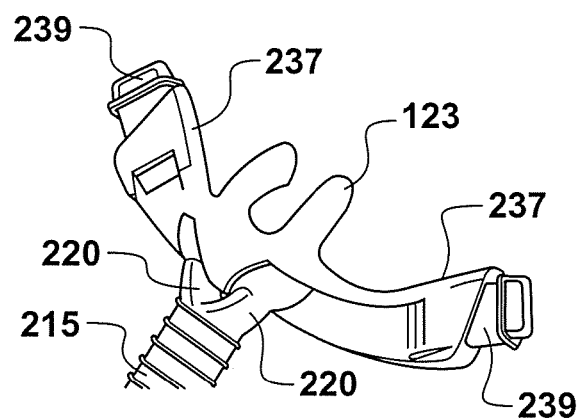
Figure 22:
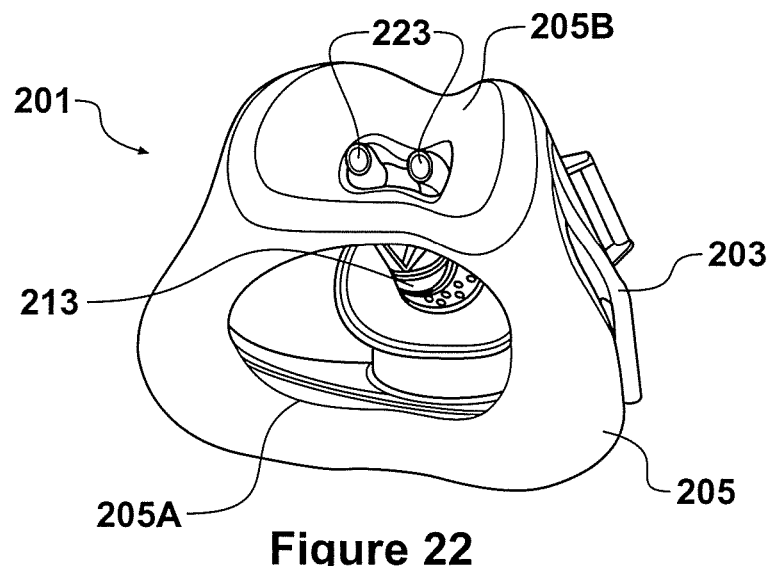
FIG. 22 is a perspective view of another embodiment of a respiratory user interface in accordance with the present disclosure.
Figure 23A:
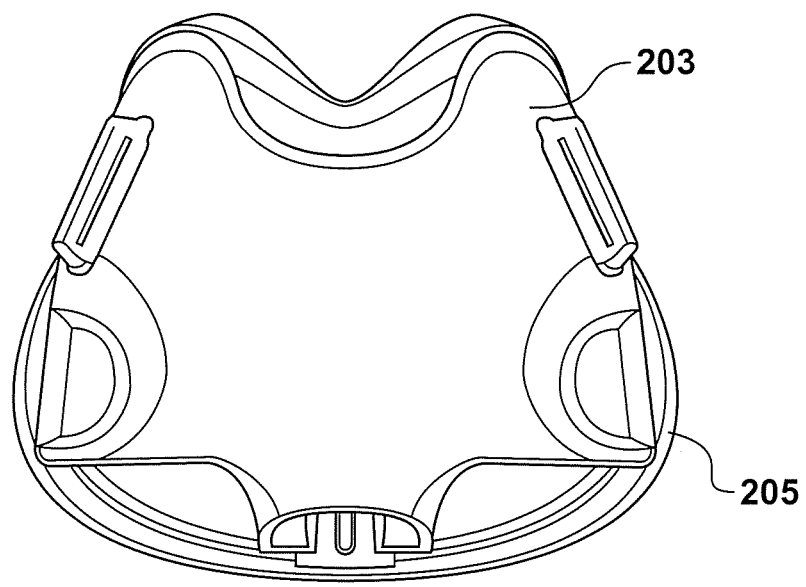
FIGS. 23a to 23e are further views of the user interface of FIG. 22.
Figure 23B:
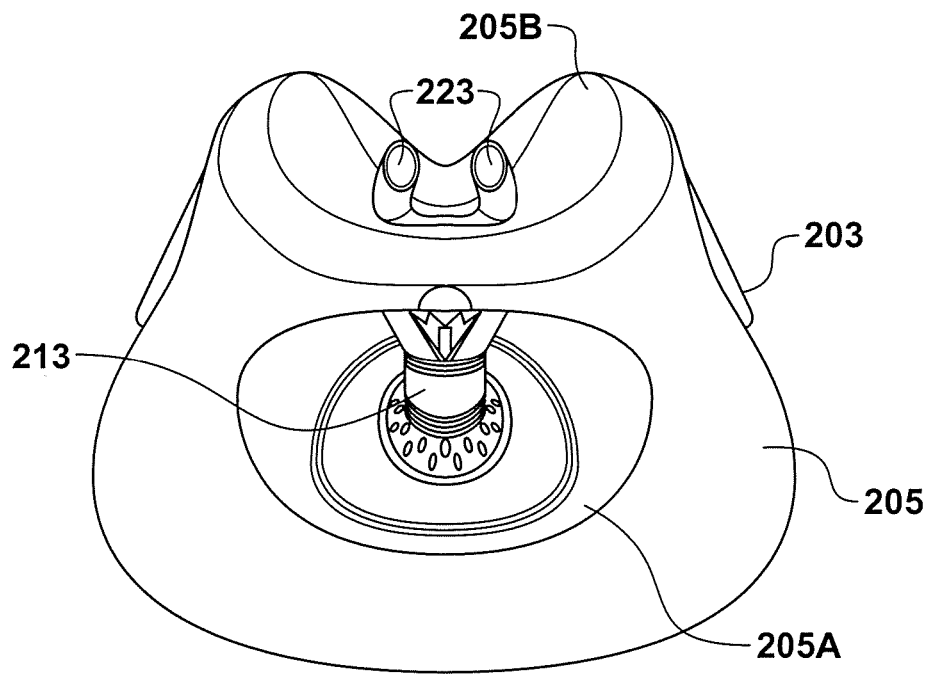
Figure 23C:
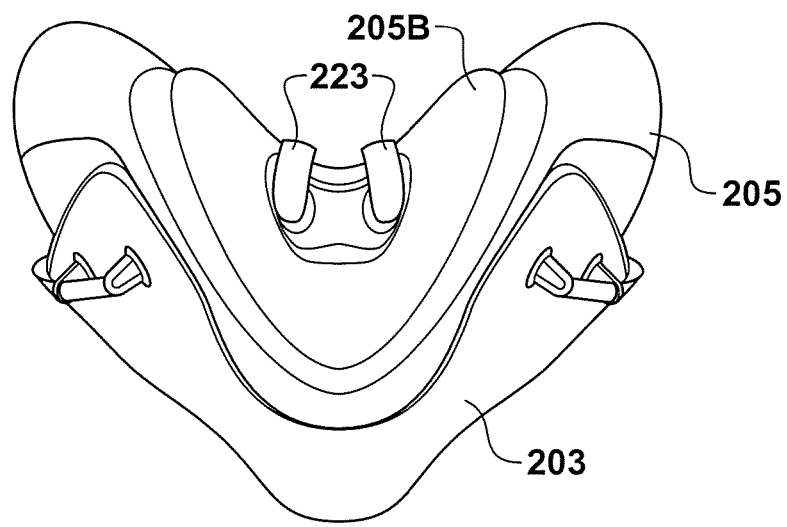
Figure 23D:
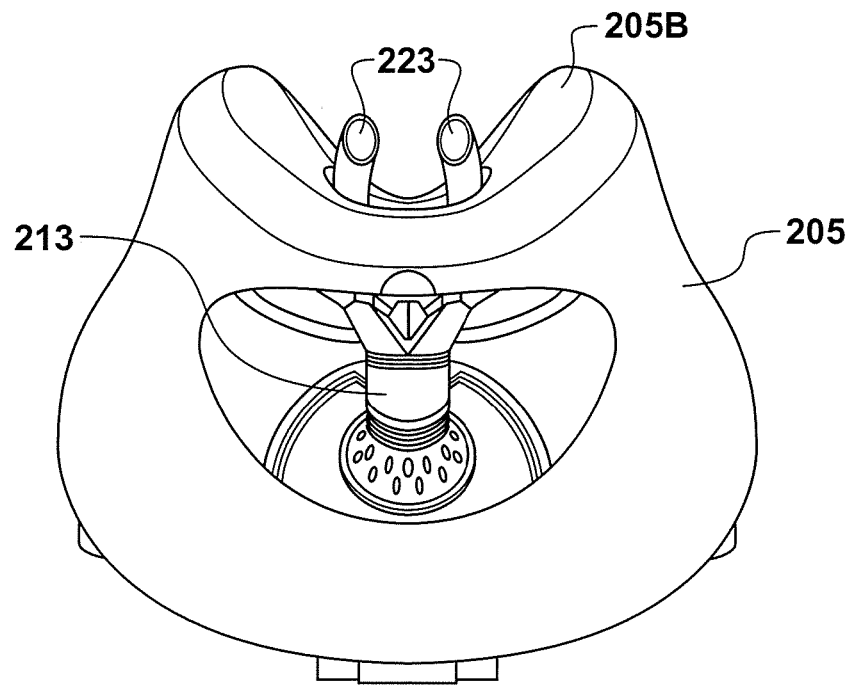
Figure 23E:
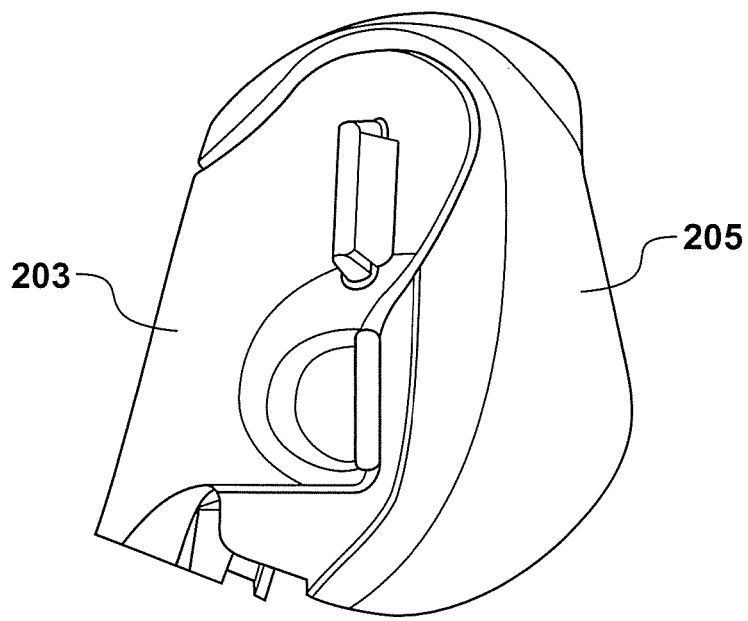
Figure 24:
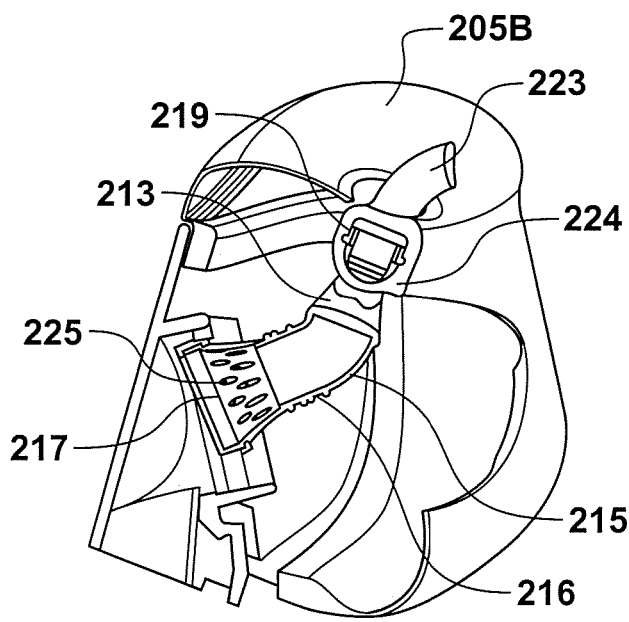
FIG. 24 is a sectional side view of the user interface of FIGS. 22 and 23.
Figure 25A:
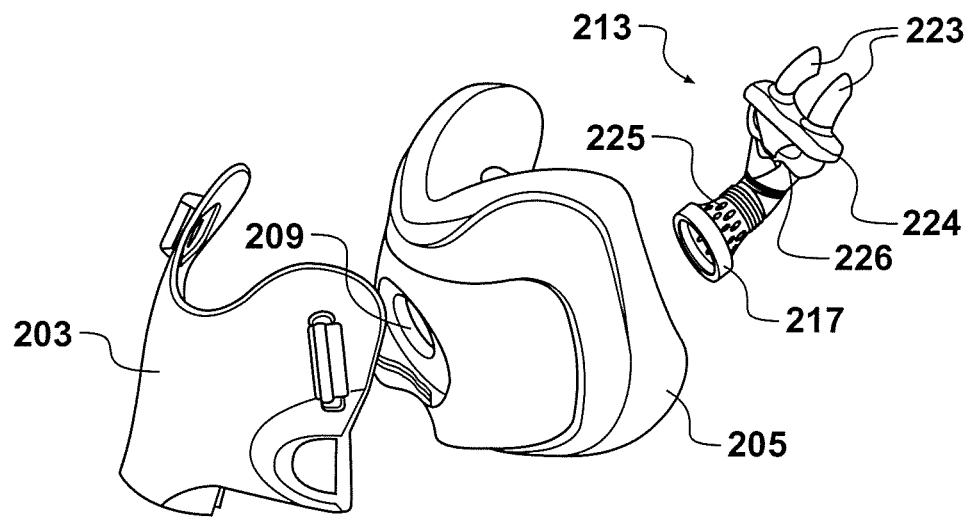
FIGS. 25a and 25b are exploded perspective views of the user interface of FIGS. 22 to 24.
Figure 25B:
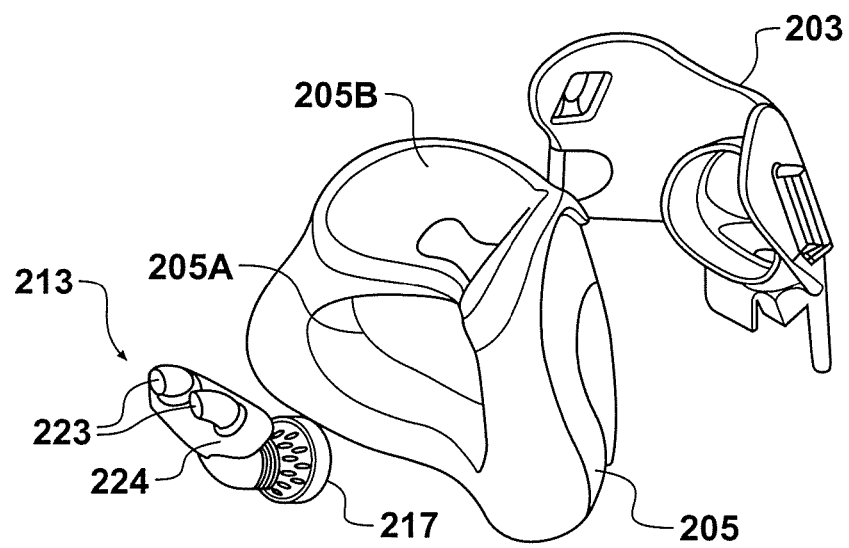
Figure 26:
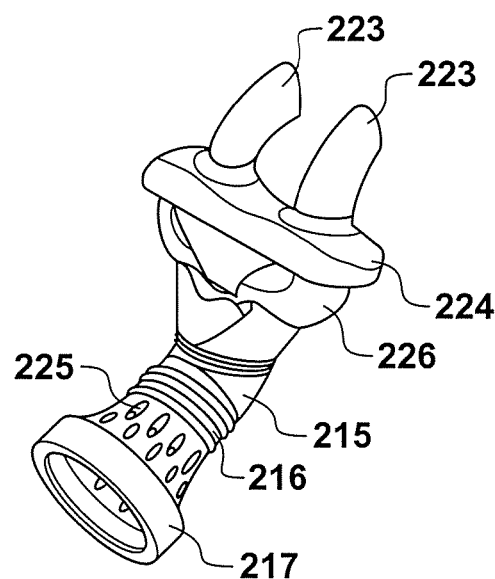
FIG. 26 is a perspective view of a gas flow director comprising part of the user interface of FIGS. 22 to 25.
Figure 27A:
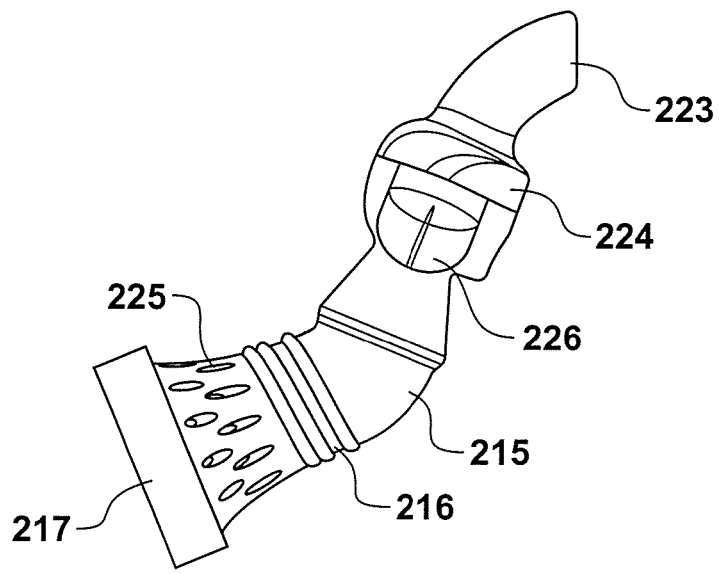
FIGS. 27a to 27c are further views of the gas flow director of FIG. 26.
Figure 27B:
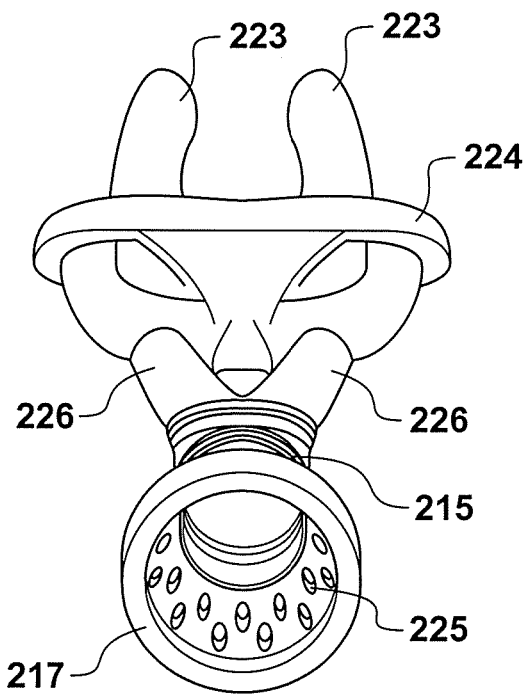
Figure 27C:
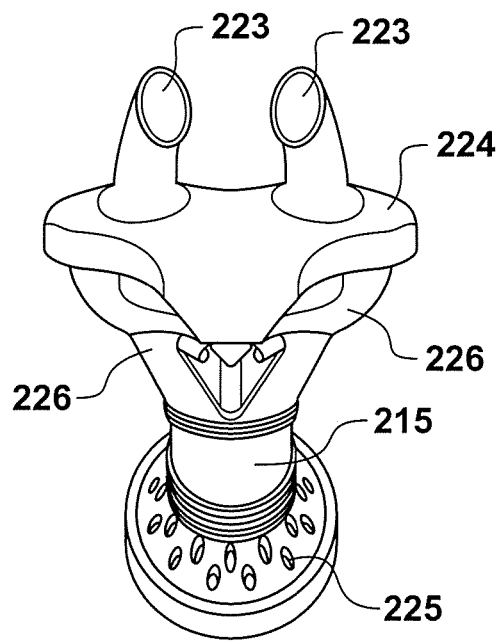
Figure 28:
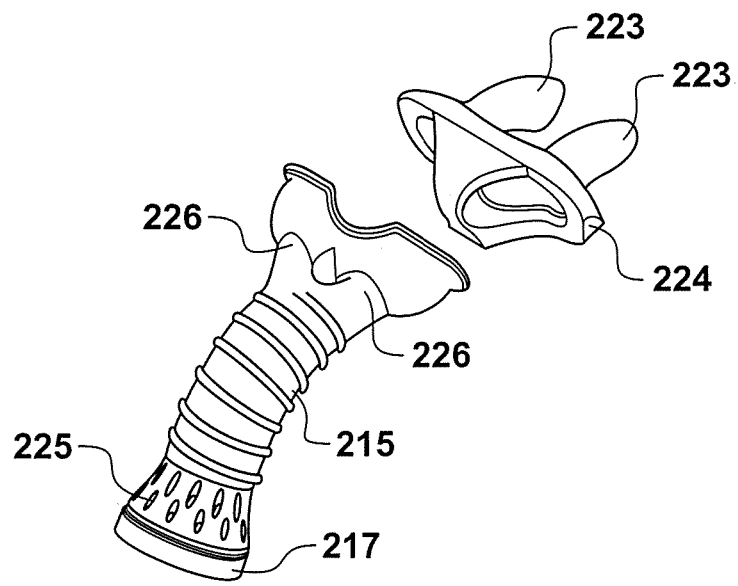
FIG. 28 is an exploded perspective view of the gas flow director of FIGS. 26 and 27.
Figure 29:
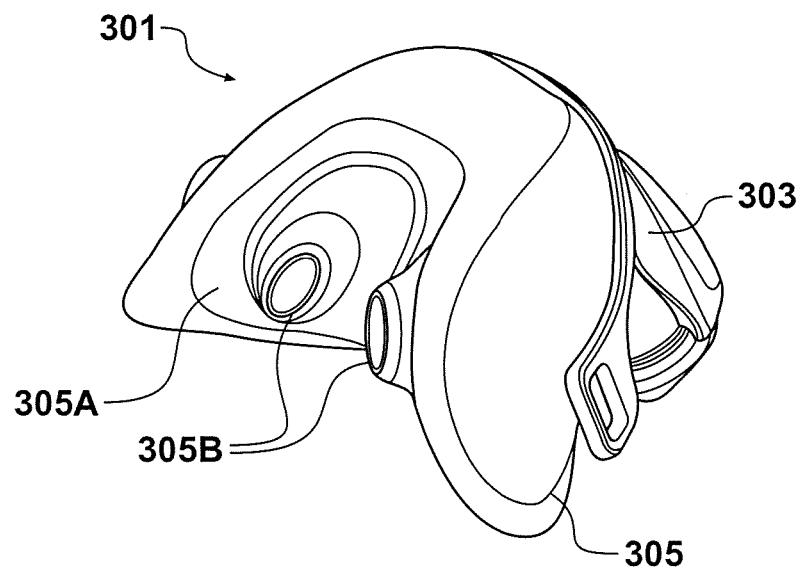
FIG. 29 is a rear perspective view of another embodiment of a respiratory user interface in accordance with the present disclosure.
Figure 30:
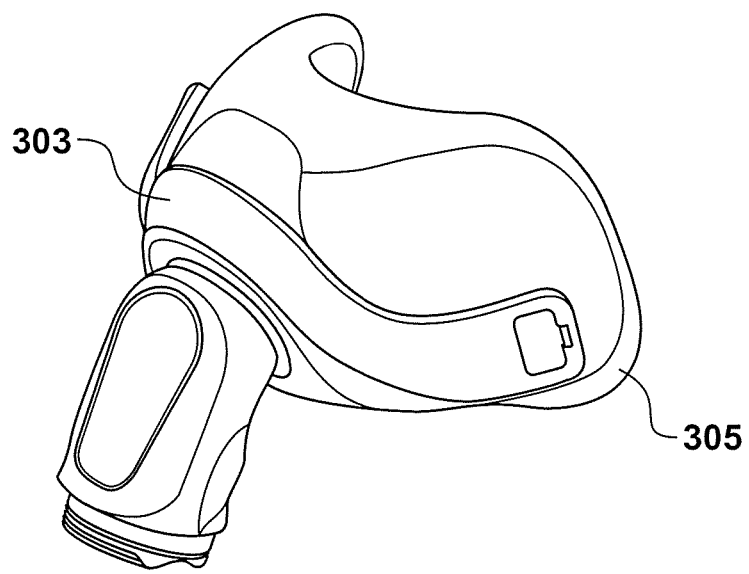
FIG. 30 is a front perspective view of the respiratory user interface of FIG. 29.
Figure 31A:
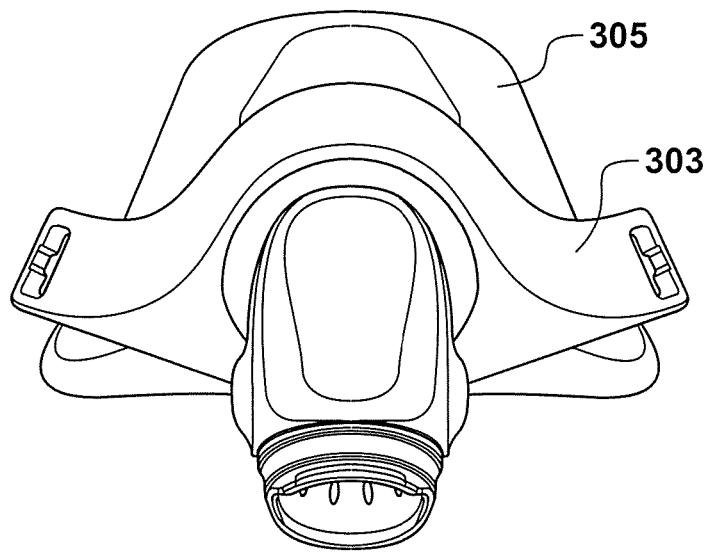
FIGS. 31a to 31d are further views of the user interface of FIG. 22.
Figure 31B:
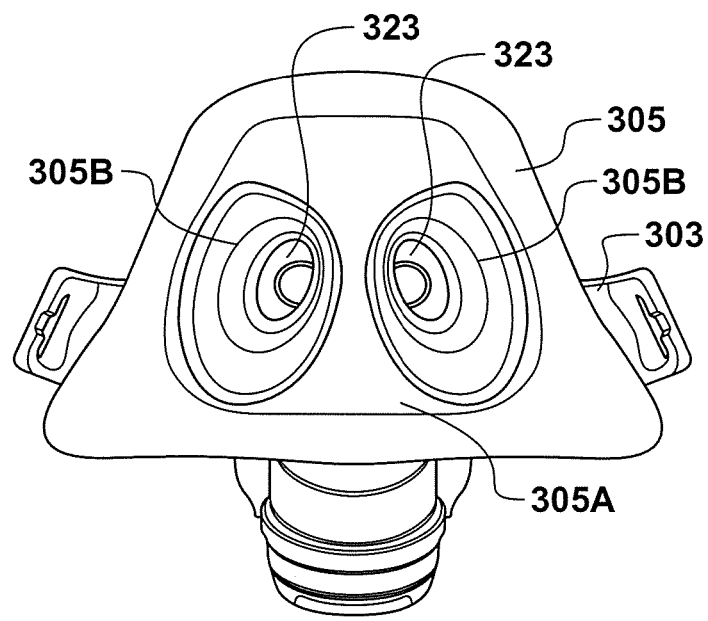
Figure 31C:
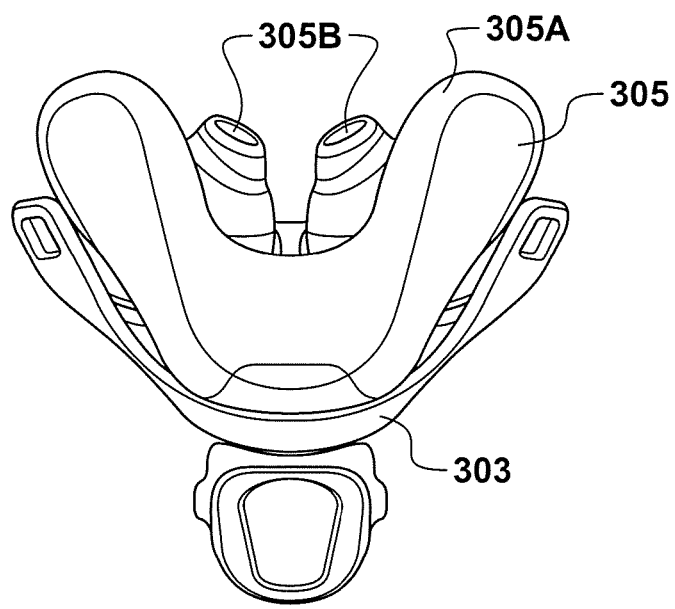
Figure 31D:
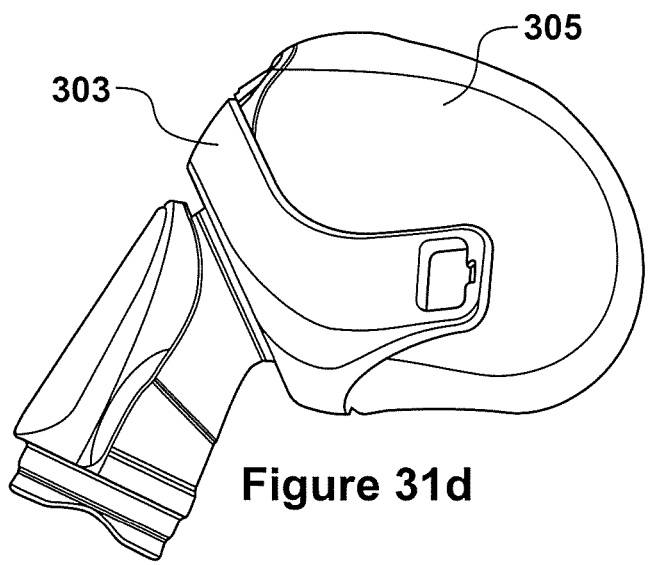
Figure 32:
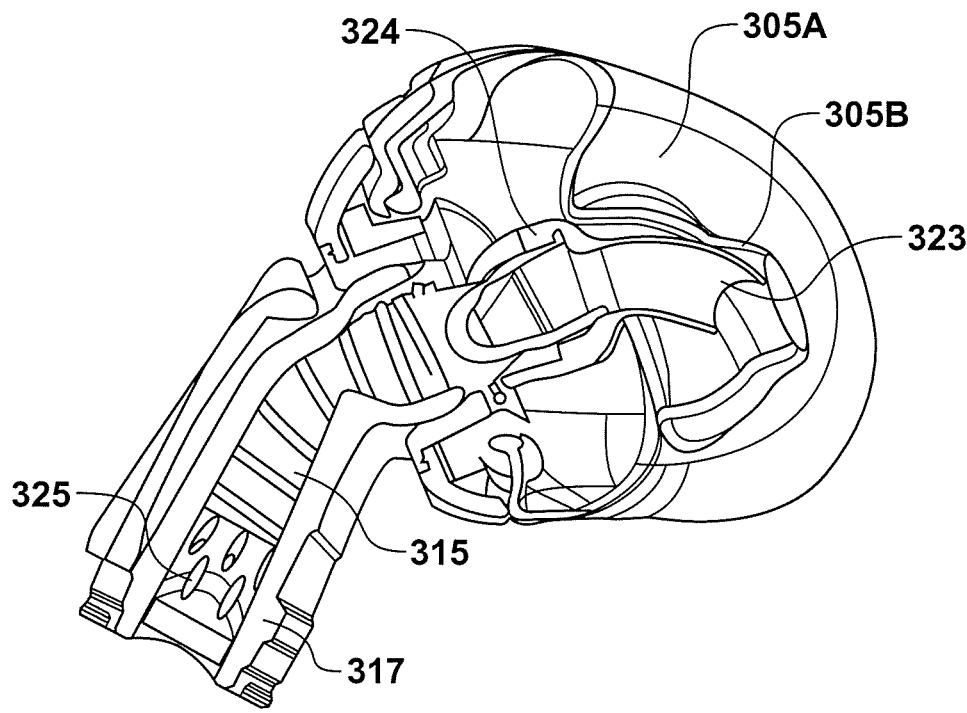
FIG. 32 is a sectional side view of the user interface of FIGS. 22 and 23.
Figure 33A:
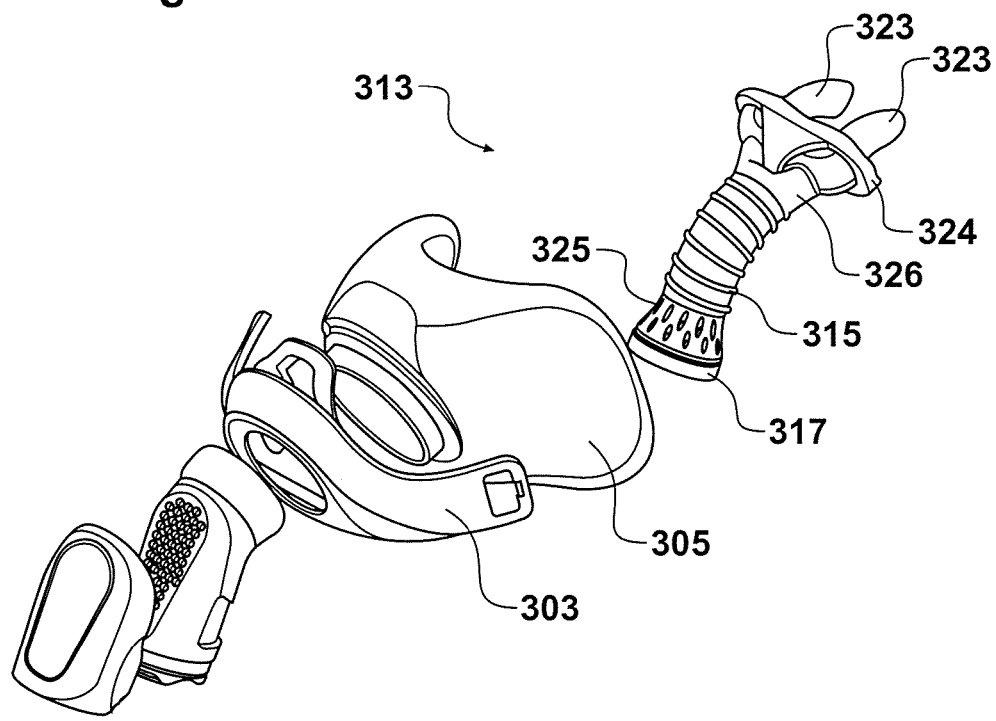
FIGS. 33a and 33b are exploded perspective views of the user interface of FIGS. 22 to 24.
Figure 33B:
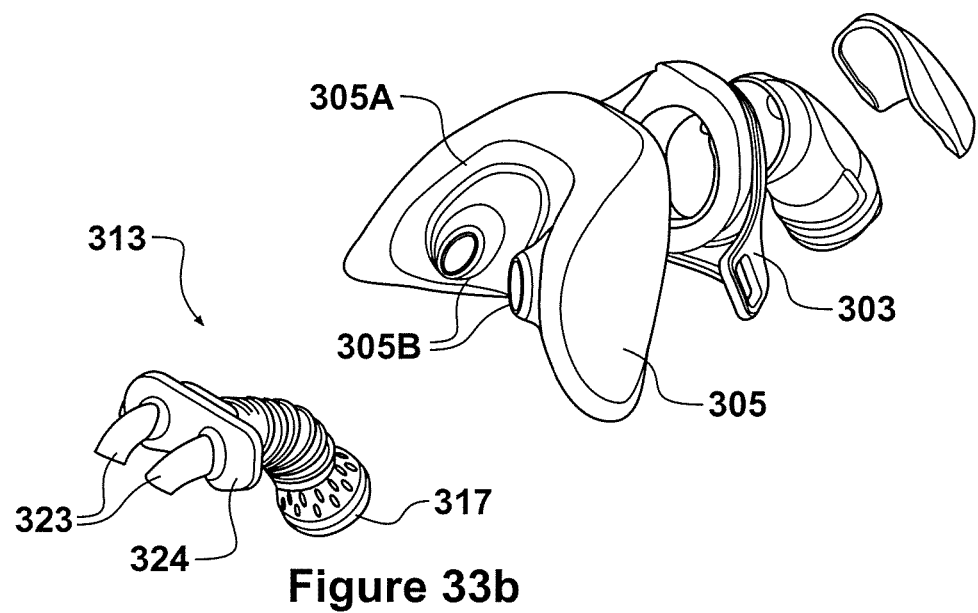
Figure 34:
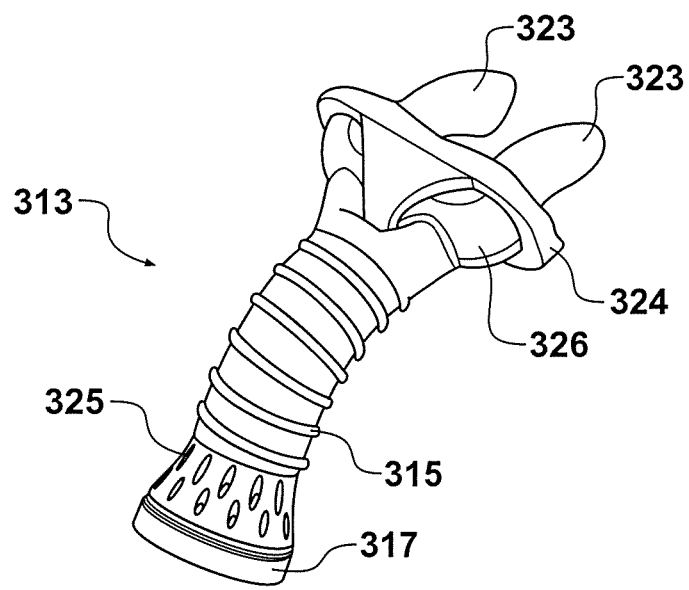
FIG. 34 is a perspective view of a gas flow director comprising part of the user interface of FIGS. 22 to 25.
Figure 35A:
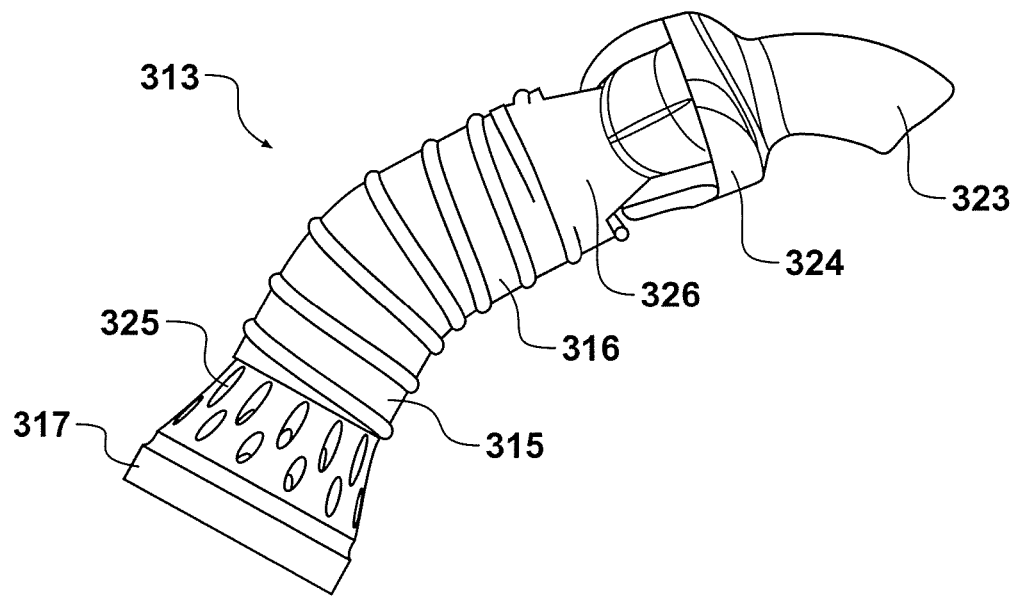
FIGS. 35a to 35c are further views of the gas flow director of FIG. 26.
Figure 35B:
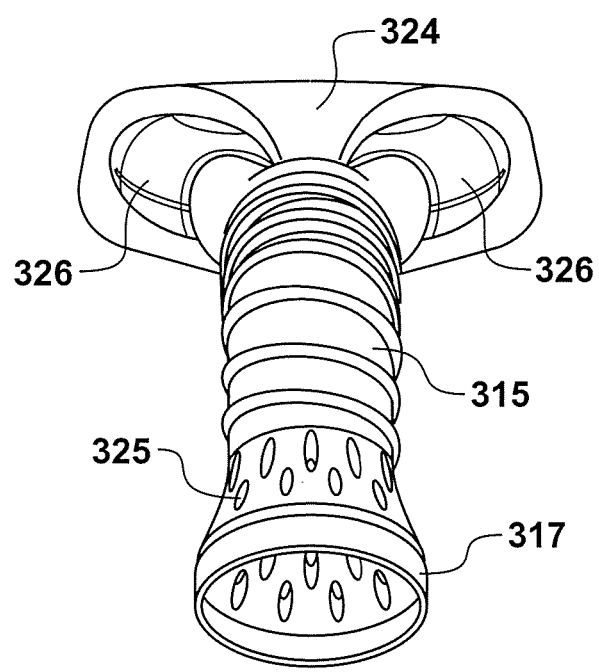
Figure 35C:
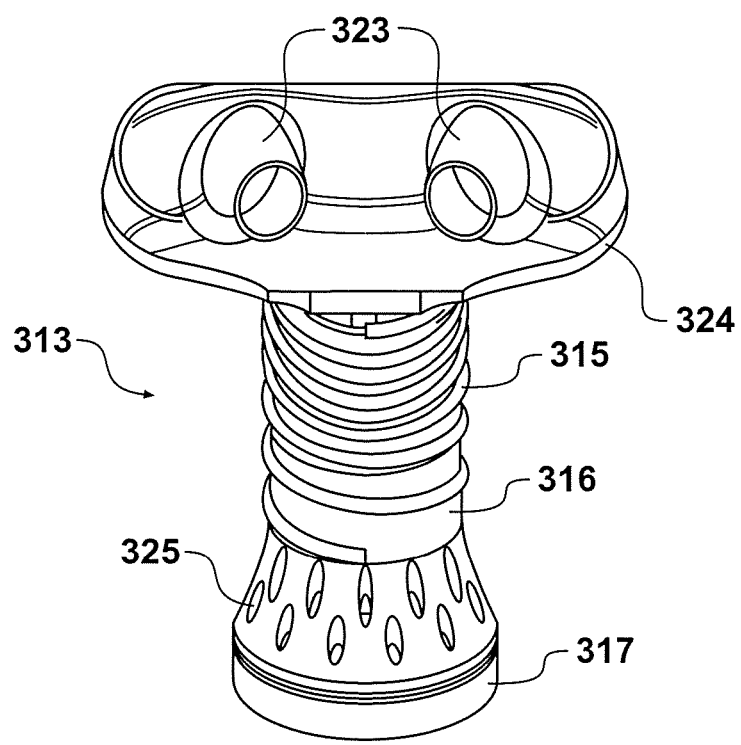

In an alternate configuration of assembly 213 of FIG. 21a, the duct 215 meets the nasal cannula manifold 235 at a single point, where the flow is then diverted into each nasal prong 123 via the manifold 235. In the configuration of assembly 213 of FIG. 21b, the duct 215 bifurcates into first and second channels 220 prior to contacting the nasal cannula manifold 235, where the divided airflow is directed from each channel 220 into respective nasal prongs 123.

In the illustrated configuration, each arm vent inlet is a single hole, and each arm vent outlet is a single hole. This need not necessarily be the case. Each arm vent inlet and arm vent outlet may comprise a number of holes arranged in a way that minimizes sound and flow perturbations.

With reference to FIGS. 22 to 28, a user interface 201 comprises, in this example, a under-nose seal face mask comprising a rigid or semi-rigid mask body 203 to which a relatively soft and flexible mask cushion 205 is attached. The mask cushion 205 is configured, by a combination of shape and material selection, to comprise a mouth seal portion 205A and a nose seal portion 205B. Mouth seal portion 205A forms a seal around the user's mouth in use, to resist pressurised gas in the user interface 201 from leaking between the cushion 205 and the user's face. Nose seal portion 205B forms a seal around the underside of the user's nose. Both seal portions 205A, 205B are exposed to the interior space or chamber defined by the mask body 203 and mask cushion 205. The mouth seal portion 205A is orientated at approximately 90° or less to nose seal portion 205B, so as to be at a relative angle to comfortably and effectively seal against both the user's nose and mouth. As with the earlier examples, the mask body 203 is provided with a breathing gas inlet 209 in the form of an inlet aperture. In this example, the mask body 203 is provided with connections for providing a four point connection with headgear. In other examples other types of headgear connection can be provided, such as a two point connection for example.

As with the earlier examples, a breathing gas flow director and nasal cannula assembly 213 is mounted inside the user interface 201 in the interior space or chamber defined by the mask body 203 and mask cushion 205. The assembly 213 is mounted to the mask body 203, or to a frame to which the mask body 203 is mounted. The assembly 213 is substantially similar to assembly 113 described above, and comprises an elongate duct 215 of serpentine form comprising a relatively narrow diameter middle or waist region 216, which flares radially outwardly to define a wider diameter breathing gas inlet end 217 and an opposed breathing gas outlet end.

The outlet end terminates in a nasal cannula comprising a pair of non-sealing nasal prongs 223 which project from the outlet end and are shaped and dimensioned to be received in a user's nares, but not to seal with the nares. Thus the prongs 223 are configured such that a gas leak path is defined around the prongs 223 when inserted into the user's nares. The prongs 223 project into the nose sealing portion 205B through the nasal aperture of respective nares. A gas leak path is defined in each nare, around the prongs such that gas can leak from each nare through the nasal apertures. In this example, the prongs 223 are provided on a manifold 224 of the assembly 213, the manifold 224 fluidly coupling with a bifurcated conduit portion 226 which is in fluid communication with a main gas delivery conduit portion comprising duct regions 215, 216, which extend from outwardly flared inlet end 217.

The assembly 213 further comprises at least one vent aperture and in this example, an array of a plurality of internal vent apertures or supplementary flow apertures 225. The apertures 225 in this example are provided on the outwardly flared inlet end 217 of duct 215, and extend around the circumference of inlet end 217.

The inlet end 217, the outlet end and nasal prongs 223, and the vent apertures 225, together provide two breathing or inspiratory gas flow paths along which breathing gas can flow from the user interface inlet 209. The first flow path delivers breathing gas directly to the nares of the user. The second gas flow path deliver breathing gas to the interior space or chamber defined by the mask body 203 and mask cushion 205. The first flow path therefore delivers breathing gases directly to the user's nares, whilst the second flow path pressurises the interior of the user interface 201 and indirectly delivers pressurised gases to both the mouth and nose of the user. The leak around the prongs 223 also contributed to the pressure in the interior chamber of the user interface 201.

With reference to FIGS. 29 to 35, a user interface 301 comprises, in this example, a nasal pillows type mask comprising a rigid or semi-rigid mask body 303 to which a relatively soft and flexible mask cushion 305 is attached. The mask cushion 305 is configured, by a combination of shape and material selection, to comprise only a nose seal portion 305A, configured to seal around the underside of the user's nose. The nose seal portion 305A further comprises a pair of nasal pillows 305B configured by shape and material selection to seal inside respective nares of the user. The pillows 305B may be configured to inflate in use, to form a seal against the user's nares. Nose seal portion 305A and nasal pillows 305B are exposed to the interior space or chamber defined by the mask body 303 and mask cushion 305.

As with the earlier examples, a breathing gas flow director and nasal cannula assembly 313 is mounted inside the user interface 301 in the interior space or chamber defined by the mask body 303 and mask cushion 305. The assembly 313 is substantially similar to assembly 213 described above. Prongs 323 project into nasal pillows 305B, but not beyond nasal pillows 305B, as can best be seen in FIG. 32.

The inlet end 317, the outlet end 319 and nasal prongs 323, and the vent apertures 325, together provide two breathing or inspiratory gas flow paths along which breathing gas can flow from the user interface inlet 309. The first flow path delivers breathing gas directly to the nares of the user. The second gas flow path deliver breathing gas to the interior space or chamber defined by the mask body 303 and mask cushion 305. The first flow path therefore delivers breathing gases directly to the user's nares, whilst the second flow path pressurises the interior of the user interface 301.

In this example the assembly 113 is mounted in elbow 111, with the lower end of assembly 113 engaging with, and being retained by, complementary formations at the lower end of elbow 111. The assembly 113 can be retained in the elbow using any other type or position of complimentary formation. The engagement between the assembly 113 and elbow 111 is such that the assembly 113 can move with the elbow 111, and can rotate with the elbow 111 if the elbow is rotatable. The assembly is also of sufficient flexibility to enable the assembly to move with the elbow. The vent apertures 325 are located inside the interior passage of the elbow 111 such that a gases flow path is defined between the interior of the elbow 111 and the interior of the assembly 113.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Although this invention has been described by way of example and with reference to possible embodiments thereof, it is to be understood that modifications or improvements may be made thereto without departing from the scope of the invention. The invention may also be said broadly to consist in the parts, elements and features referred to or indicated in the specification of the application, individually or collectively, in any or all combinations of two or more of said parts, elements or features. Furthermore, where reference has been made to specific components or integers of the invention having known equivalents, then such equivalents are herein incorporated as if individually set forth.

Any discussion of the prior art throughout the specification should in no way be considered as an admission that such prior art is widely known or forms part of common general knowledge in the field.

The invention claimed is:
1. A user interface comprising:
 a mask body and a sealing cushion connected to the mask body and configured to seal around a patient's nose and/or a patient's mouth; wherein the mask body and sealing cushion together define an interior chamber of the user interface;
 a breathing gas delivery inlet configured to receive a breathing gas flow from a gas source;
 a nasal prong assembly comprising a manifold and at least one non-sealing nasal prong in the interior chamber, wherein the at least one non-sealing nasal prong extends from the manifold of the nasal prong assembly;

wherein the user interface further comprises a breathing gas flow director configured to split the breathing gas flow into a first flow path and a second flow path, such that a first portion of the breathing gas flow is delivered along the first flow path from the breathing gas delivery inlet into the interior chamber to pressurize the interior chamber, and such that a second portion of the breathing gas flow is delivered along the second flow path from the breathing gas delivery inlet through the at least one non-sealing nasal prong; and wherein the nasal prong assembly comprises at least one laterally extending arm which extends from the manifold such that a distal end of the at least one laterally extending arm projects externally of the mask body, the distal end comprising a vent outlet, the at least one laterally extending arm defining a vent passage through a portion of the at least one laterally extending arm, the vent passage being in fluid communication with the interior chamber and the vent outlet.

2. The user interface of claim 1 comprising a nasal seal configured to seal around a patient's nares or the patient's nose.

3. The user interface of claim 2 comprising a nasal seal portion configured to seal around an underside of the patient's nose.

4. The user interface of claim 2 comprising a pair of nasal pillows configured to be received in, and seal against, the patient's nares.

5. The user interface of claim 4 wherein each nasal pillow is associated with a respective one of the at least one non-sealing nasal prong which extends into the pair of nasal pillows.

6. The user interface of claim 5 wherein each of the at least one non-sealing nasal prong does not project beyond the pair of nasal pillows.

7. The user interface of claim 1 comprising a full face seal configured to seal around both the patient's mouth and the patient's nose.

8. The user interface of claim 7 comprising a single seal opening, exposed to the interior chamber, and configured to seal around the patient's mouth and the patient's nose.

9. The user interface of claim 7 comprising a nasal seal opening configured to seal around an underside of the patient's nose, and a mouth seal opening configured to seal around the patient's mouth, both the nasal seal opening and the mouth seal opening being exposed to the interior chamber.

10. The user interface of claim 9, wherein the vent passage comprises a vent inlet, configured to be exposed to gases in the interior chamber of the mask body, the vent inlet being spaced from the vent outlet.

11. The user interface of claim 10, wherein the vent inlet is positioned part way along the at least one laterally extending arm, distal from both the vent outlet and the nasal seal opening or distal from the vent outlet but adjacent the nasal seal opening.

12. The user interface of claim 1, wherein the vent outlet is provided on a side part of the mask body, to one side of the breathing gas delivery inlet, and/or comprises a plurality of mask vent holes, and/or projects through the sealing cushion.

13. The user interface of claim 1, wherein the vent outlet is oriented so as to direct vented gases away from a patient's face and/or to direct vented gases upwardly and/or forwardly, or downwardly, or laterally, with respect to an orientation of the user interface in normal use.

14. The user interface of claim 1, wherein the vent passage comprises a vent inlet, configured to be exposed to gases in the interior chamber of the mask body, the vent inlet being spaced from the vent outlet.

15. The user interface of claim 14, wherein the vent inlet is positioned part way along the at least one laterally extending arm, distal from both the vent outlet and the at least one non-sealing nasal prong or distal from the vent outlet but adjacent the at least one non-sealing nasal prong.

16. The user interface of claim 1, wherein the vent outlet and the vent passage are comprised in an arm vent assembly, the arm vent assembly being attached to the distal end of the at least one laterally extending arm, and/or wherein the arm vent assembly is attached to the distal end of the at least one laterally extending arm via any one or more of:
   an interference fit;
   a snap-fit;
   overmoulding
   co-moulding the arm vent assembly and the at least one laterally extending arm.

17. The user interface of claim 1, wherein the vent passage is largely rectangular in transverse cross section and extends laterally within the at least one laterally extending arm.

18. The user interface of claim 1, wherein the at least one non-sealing nasal prong of the user interface comprises non-sealing nasal cannula or non-sealing nasal high flow nasal cannula.

19. The user interface of claim 1, further comprising any one or more of:
   a breathing gas flow generator;
   a breathing gas humidifier; and/or
   a gas delivery conduit, which may or may not be heated.

20. A user interface comprising:
   a mask body and a sealing cushion connected to the mask body and configured to seal around a patient's nose and/or a patient's mouth; wherein the mask body and sealing cushion together define an interior chamber of the user interface;
   a breathing gas delivery inlet configured to receive a breathing gas flow from a gas source;
   at least one non-sealing nasal prong in the interior chamber; and
   wherein the user interface further comprises a breathing gas flow director configured to split the breathing gas flow into a first flow path and a second flow path, such that a first portion of the breathing gas flow is delivered along the first flow path from the breathing gas delivery inlet into the interior chamber to pressurize the interior chamber, and such that a second portion of the breathing gas flow is delivered along the second flow path from the breathing gas delivery inlet through the at least one non-sealing nasal prong; and
   wherein the user interface also comprises at least one laterally extending arm which extends from the interior chamber such that a portion of a distal end of at least one laterally extending arm projects externally of the mask body, the distal end of each of the at least one laterally extending arm comprising a vent outlet and a vent inlet, the at least one laterally extending arm defining a vent passage through a portion of the at least one laterally extending arm, the vent passage being in fluid communication with the interior chamber and the vent outlet.

* * * * *